United States Patent
Huger et al.

(10) Patent No.: US 12,240,936 B2
(45) Date of Patent: *Mar. 4, 2025

(54) POLYURETHANE WITH DELAYED RELAXATION BEHAVIOUR FOR COMPRESSION PRODUCTS

(71) Applicant: MEDI GMBH & CO. KG, Bayreuth (DE)

(72) Inventors: Christa Huger, Kulmbach (DE); Angelika Scherm, Immenreuth (DE); Seema Agarwal, Marburg (DE); Andreas Greiner, Amöneburg (DE); Pin Hu, Bayreuth (DE)

(73) Assignee: MEDI GMBH & CO. KG, Bayreuth (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/222,433

(22) Filed: Jul. 15, 2023

(65) Prior Publication Data

US 2024/0002573 A1 Jan. 4, 2024

Related U.S. Application Data

(63) Continuation of application No. 16/636,493, filed as application No. PCT/EP2018/071535 on Aug. 8, 2018, now Pat. No. 11,746,179.

(30) Foreign Application Priority Data

Aug. 9, 2017 (EP) ..................................... 17185611

(51) Int. Cl.
| | |
|---|---|
| *C08G 18/24* | (2006.01) |
| *A61F 13/08* | (2006.01) |
| *C08G 18/08* | (2006.01) |
| *C08G 18/32* | (2006.01) |
| *C08G 18/38* | (2006.01) |
| *C08G 18/48* | (2006.01) |
| *C08G 18/66* | (2006.01) |
| *C08G 18/76* | (2006.01) |
| *C08L 75/04* | (2006.01) |

(52) U.S. Cl.
CPC .......... *C08G 18/0814* (2013.01); *A61F 13/08* (2013.01); *C08G 18/246* (2013.01); *C08G 18/3206* (2013.01); *C08G 18/3821* (2013.01); *C08G 18/4854* (2013.01); *C08G 18/6685* (2013.01); *C08G 18/7671* (2013.01); *C08L 75/04* (2013.01); *C08G 2280/00* (2013.01); *C08L 2201/12* (2013.01); *C08L 2203/02* (2013.01); *C08L 2205/025* (2013.01); *C08L 2205/03* (2013.01)

(58) Field of Classification Search
USPC ............................ 528/44, 49, 68, 95; 602/75
See application file for complete search history.

(56) References Cited

U.S. PATENT DOCUMENTS

| | | | |
|---|---|---|---|
| 3,853,804 A | 12/1974 | Yen et al. | |
| 2008/0025933 A1* | 1/2008 | Mougin | C08G 18/0814 424/70.17 |
| 2017/0051436 A1* | 2/2017 | Waldbauer, Jr. | D01D 5/04 |
| 2018/0298140 A1* | 10/2018 | Liu | C08G 18/10 |

FOREIGN PATENT DOCUMENTS

| | | |
|---|---|---|
| CN | 101392049 A | 3/2009 |
| CN | 103232587 A | 4/2013 |
| CN | 205924313 U | 2/2017 |
| DE | 4040156 A1 | 6/1992 |
| JP | 11255845 A | 9/1999 |
| JP | 2013168258 A | 8/2013 |
| JP | 2017500133 A | 1/2017 |
| WO | 2015094792 A1 | 6/2015 |

OTHER PUBLICATIONS

Jian et al., "Synthesis and Characterizations of New Lysine-Based Biodegradable Cationic Poly(urethane-co-ester) and Study on Self-Assembled Nanoparticles with DNA," Bioconjugate Chem vol. 20, No. 4, pp. 775-779, Dec. 31, 2009.
First Examination Report issued by the Chinese Patent Office on Aug. 4, 2021 with respect to the parallel Chinese Application No. 201880051055.1 with English translation.
Japanese Office Action issued by the Japanese Patent Office on Aug. 2, 2022 with respect to the parallel Japanese Application No. 2020-506775 with English translation.

* cited by examiner

*Primary Examiner* — Terressa Boykin
(74) *Attorney, Agent, or Firm* — SALIWANCHIK, LLOYD & EISENSCHENK

(57) ABSTRACT

The invention relates to medical aids, in particular compression products, such as compression stockings or bandages. Specifically, the invention provides a compression product comprising an elastic component or material that comprises polyurethane polymers and shows a delayed continuous relaxation behaviour. The invention furthermore provides polyurethane polymers containing N-diol having a delayed continuous relaxation behavior and corresponding quaternized polyurethane polymers, a process for producing the polyurethane polymers, a blend with elastane, as well as uses thereof.

19 Claims, 21 Drawing Sheets

Does not come back to original length (500x magnification)

POLYURETHANE WITH DELAYED RELAXATION BEHAVIOUR FOR COMPRESSION PRODUCTS

CROSS REFERENCE TO RELATED APPLICATIONS

This application is a continuation application of U.S. patent application Ser. No. 16/636,493, filed Feb. 4, 2020, now U.S. Pat. No. 11,746,179; which is a National Stage Application of International Application Number PCT/EP2018/071,535, filed Aug. 8, 2018; which claims priority to European Patent Application No. 17185611.5, filed Aug. 9, 2017.

FIELD OF THE INVENTION

The invention relates to medical aids, in particular compression products, such as compression stockings or bandages. More specifically, the invention relates to compression products comprising fibre forming polyurethane polymers showing a delayed continuous relaxation behaviour. The invention furthermore relates to polyurethane polymers containing N-diol and corresponding quaternised polyurethane polymers, to a process of producing the polyurethane polymers, to blends with elastane, as well as to uses.

BACKGROUND OF THE INVENTION

State of the Art

Compression stockings are a specialised hosiery designed to help prevent the occurrence of, and to guard against further progression of, venous disorders, such as oedema, phlebitis and thrombosis. Such stockings are elastic garments worn around the leg, thereby compressing the limb. This reduces the diameter of distended veins and increases venous blood flow velocity and valve effectiveness.

In the clinical or ambulatory setting, the applying of compression stockings usually is performed by a physician or nurse. Alternatively, compression stockings are applied by patients themselves, for example at home, also on a daily basis.

Fit is critical to the therapeutic effect of compression stockings. Therefore, the proper sized stocking is first determined by measuring the legs. The correct application of compression stockings may also be critical, which is why medical personnel or the patient needs to be trained carefully.

Due to the compression intended to be provided to the leg, the material compression stockings are made of must not be too elastic and expansible, and thus compression stockings can be hard to put on. This is particularly true in cases where the patient is weak, bedridden or invalid, or has to experience pain.

Thus, the development of compression stockings and other medical compression products that ensure good compression, while at the same time are comfortable to apply, is still challenging.

Usually, elastic polymers incorporated in the compression products are the target of efforts of improvement. One popular polymer often used when elasticity is desired is elastane.

Elastane (spandex, Lycra®) is a polyether-polyurea block copolymer containing at least 85% polyurethane. It was invented in 1958 at DuPont's and introduced onto the market in 1962. Synthetic fibres of elastane are known for their exceptional elasticity: After being strongly expanded, an elastane fibre virtually recovers its original length. Insofar, elastane is an elastomer like natural rubber, but is stronger and more durable. Apart from medical compression products, elastane is widely used in textile and clothing industry, e.g. in tights, corsetry articles or sportswear.

US 2008/0249454 discloses compression stockings constructed from a knit fabric comprising a taut elastic material providing sufficient stretch to allow the stockings to be easily placed on a foot. Spandex is a material considered to be incorporated in the stockings.

WO 2011/132011 discloses a knitted-type compression item with a therapeutic and/or physiological effect, designed for facilitating the pulling-on thereof, with a high level of compression of more than 20 mmHg, comprising a double-helix plated weft yarn with an elastomer core, especially elastane, over the entirety of the item produced.

Several other elastic polymers are also used in compression products, polyurethane being one of them. Polyurethane (PU) is a polymer made of a multitude of molecular units, which are joined by urethane (carbamate) groups. Basically, the polymer is produced through step polymerisation (polyaddition), in which process a monomer containing at least two isocyanate functional groups (—N=C=O) reacts with another monomer containing at least two hydroxyl (alcohol) (—OH) groups, thereby forming the urethane group (—NH—CO—O—).

US 2007/0113593 discloses functional compression socks comprising polyurethane.

US 2010/0191163 discloses a dynamic-response anatomical bandaging system comprising a polyurethane foam layer.

An interesting approach in the improvement of compression products is the usage of shape memory polymers. Shape memory materials are featured by the ability to recover their original shape from a significant and seemingly plastic deformation when a particular stimulus is applied (shape memory effect). After deformation by stretching, fibres of shape memory polymers can be triggered for shape recovery by various stimuli, such as light (UV and infrared light), chemical stimuli (moisture, solvent, pH change), heat (e.g., in thermo-responsive shape memory polymers), an electric or magnetic field, or radiation. The idea behind the usage of shape memory polymers is that the compression product can be applied in a temporarily preserved expanded shape. Upon the appropriate stimulus, the compression product eventually relaxes, i.e., reverses the deformation, thereby building up a compression.

WO 2012/045427 discloses medical aids, in particular body support bandages and orthotics, for the human or animal body, comprising at least one element which generates or delivers a supporting force, compression, or introduction of pressure, and which comprises shape memory material or consists thereof. Polyurethane is contemplated as the shape memory material. The shape memory effect is triggered by body temperature.

WO 2013/149985 discloses a knitted fabric containing a shape memory material and a swelling agent. Polyurethane is considered to serve as the shape memory material.

CN 105078652 discloses an intelligent compression system based on shape memory material.

In any case, high standards are to be demanded of elastic polymers for use in medical compression products. They shall provide good compression and, at the same time, involve good application properties. Additionally, they should show excellent tensile strength, compatibility with medical applications, skin-friendliness, suitability for daily use, and good washing properties.

There is still a need for improvement of elastic polymers intended for use in medical compression products.

It is therefore an object of the invention to provide improved elastic polymers and thus improved medical compression products.

SUMMARY OF THE INVENTION

The invention achieves the object as defined in the independent claims and as described below under different aspects. Specific embodiments are defined in dependent claims and also described below.

In a first aspect, the invention provides a compression product comprising or consisting of an elastic component or material, the elastic component or material being capable of applying a compression or a supporting force or a local pressure to a part of the body of a subject, the elastic component or material furthermore being capable of passing through a first phase during which the component or material is expanded, a second phase during which the component or material relaxes without recovering or completely recovering its original shape, or only partially recovering its original shape, and a third phase during which the component or material recovers its original shape, or virtually recovers or nearly completely recovers its original shape, preferably successively recovers its original shape, more preferably recovers its original shape with successive deceleration, wherein relaxation, preferably the second phase, more preferably the second and third phases, is/are self-initiated, preferably is/are initiated autonomously or spontaneously in the absence of an external stimulus.

In one embodiment of the compression product, the elastic component or material comprises or consists of:
  (a) a non-quaternised polyurethane (PU) polymer containing N-diol (PU-N);
  and/or
  (b) a quaternised polyurethane (PU) polymer or ionomer containing quaternised N-diol (PU-N+);
  and, optionally,
  (c) elastane.

In a second aspect, the invention provides a compression product comprising or consisting of an elastic component or material comprising or consisting of:
  (a) a non-quaternised polyurethane (PU) polymer containing N-diol (PU-N);
  and/or
  (b) a quaternised polyurethane (PU) polymer or ionomer containing quaternised N-diol (PU-N+);
  and, optionally,
  (c) elastane.

In one embodiment of the first or second aspect, the compression product is a medical compression product.

In one embodiment of the first or second aspect, the compression product is selected from the group consisting of a compression hosiery, preferably a compression stocking, sock, knee sock, tights, panty hose, or maternity panty hose, a compression knee guard, a compression arm sleeve, a compression waist attachment, belt or girdle, a compression bandage, a body-supporting bandage, an orthosis, a prosthesis liner, a compression wound dressing, a compression plaster or patch, and a compression garment, preferably a compression garment for medical purposes.

In one embodiment of the second aspect, the compression product, or the elastic component or material is capable of applying a compression or a supporting force, or a local pressure to a part of the body of a subject.

In one embodiment of the first or second aspect, the part of the body is selected from the group consisting of a limb, a leg, a thigh, a lower leg, a knee, an arm, an upper arm, a forearm, an elbow, a hand, a finger, a wrist, a foot, a heel, a toe, an ankle, an Achilles tendon, a shoulder, the upper body, the lower body, the waist, the neck, a part of the head, a cheekbone, the forehead, the nose, and the chin of a subject.

In one embodiment of the first or second aspect, the subject is a human, preferably a human patient or an athlete. In an alternative embodiment, the subject is an animal, preferably a companion animal or a sport animal.

In one embodiment of the first or second aspect, the subject is the user of the medical compression product, e.g., a patient, who applies and wears the compression product. In another embodiment, a patient wears the medical compression product, which on the other hand is applied by a third person, e.g., a nurse.

In one embodiment of the first or second aspect, the compression product comprises at least one portion, or two or more portions, comprising or consisting of the elastic component or material, and at least one different portion, or two or more different portions, not containing the elastic component or material.

In one embodiment of the first or second aspect, the portion comprising or consisting of the elastic component or material is located in an area supposed to come in contact with a part of the body of a subject, which part is intended to be subjected to compression. Preferably, the part of the body is selected from the group consisting of a knee, a patella, a calf, an elbow, a wrist, a heel, a toe, an ankle, and an Achilles tendon. Optionally, the area is the ankle area or the calf area of a compression stocking, the patella area of a compression knee guard, the elbow area of a compression sleeve, or the wound area of compression wound dressing.

In one embodiment of the first or second aspect, the compression product comprises two, three or more portions which differ in the elastic component or material. Optionally, an elastic component or material in a portion located in the calf area of a compression stocking is capable of providing a stronger compression as compared to an elastic component or material in a portion located outside the calf area. Such compartmentation of a compression stocking may allow activation of the calf musco-venous pump.

In one embodiment of the first or second aspect, the compression product comprises or consists of an elastic component or material according to the invention (cf. fifth aspect).

In one embodiment of the first or second aspect, the compression product comprises or consists of elastic fibres, filaments, threads, or yarns according to the invention (cf. sixth aspect).

In one embodiment of the first or second aspect, every fibre, filament, thread, or yarn in the medical compression product comprises or consists of an elastic component or material according to the invention.

In one embodiment of the first or second aspect, the amount of elastic fibres, filaments, threads, or yarns according to the invention in the medical compression product is about 1 to 100%, about 5 to 95%, about 10 to 90%, about 20 to 80%, about 30 to 50%, about 40 to 60%, or about to 70%, related to the total amount of fibres, filaments, threads, or yarns.

In one embodiment of the first or second aspect, the compression product comprises or consists of a compressive base fabric according to the invention (cf. seventh aspect).

In one embodiment of the first or second aspect, the compression product comprises or consists of a polyurethane (PU) polymer containing N-diol according to the invention (cf. eighth or ninth aspect).

In a third aspect, the invention provides uses of a compression product according to the invention (cf. first or second aspect) in the fields of phlebology, orthopaedics, foot care, surgery, post-surgery care, trauma management, wound care, or sports.

In a fourth aspect, the invention provides uses of a compression product according to the invention (cf. first or second aspect) for treatment or prevention or management of impaired musco-venous pump performance, compromised venous circulation, venous insufficiency, preferably chronic venous insufficiency, oedema, phlebitis, thrombosis, preferably deep vein thrombosis, venous embolism, lymphoedema, ulcer, preferably ulcer of the lower leg, aching legs, varicose veins, spider veins, or the "economy class syndrome" (ECS).

In a fifth aspect, the invention provides an elastic component or material comprising or consisting of:
(a) a non-quaternised polyurethane (PU) polymer containing N-diol (PU-N);
and/or
(b) a quaternised polyurethane (PU) polymer or ionomer containing quaternised N-diol (PU-N+);
and, optionally,
(c) elastane.

In one embodiment, the elastic component or material comprises or consists of a blend of the non-quaternised PU polymer and/or the quaternised PU polymer or ionomer and elastane.

In one embodiment, the elastic component or material comprises or consists of a blend of the non-quaternised PU polymer and elastane. This embodiment is preferred.

In one embodiment, the elastic component or material comprises or consists of two or more different non-quaternised PU polymers and/or quaternised PU polymers or ionomers.

In one embodiment, the elastic component or material comprises or consists of fibres, filaments, threads, or yarns according to the invention (cf. sixth aspect). In one embodiment, such fibre, filament, thread, or yarn is treated with a powder or oil, such as $SiO_2$ powder, silicone oil or linseed oil, to prevent sticking of the fibre, filament etc., especially when it is wound up.

In one embodiment, the elastic component or material has been processed to a thread or yarn, preferably according to the invention.

In one embodiment, the elastic component or material has been processed to a textile or fabric, preferably a compressive base fabric, preferably according to the invention.

In one embodiment, the elastic component or material comprises or consists of a polyurethane (PU) polymer containing N-diol according to the invention (cf. eighth or ninth aspect).

In one embodiment, the elastic component or material is capable of passing through a first phase during which the component or material is expanded, a second phase during which the component or material relaxes without recovering or completely recovering its original shape, or only partially recovering its original shape, and a third phase during which the component or material recovers its original shape, or virtually recovers or nearly completely recovers its original shape, preferably successively recovers its original shape, more preferably recovers its original shape with successive deceleration.

In one embodiment, the elastic component or material recovers partially during the second phase by about 15 to 80%, more preferably by about 20 to 75%, optionally by about 15 to 30% or 20 to 25%, optionally by about 65 to 80 or 70 to 75% of the total length to which the elastic component or material had been expanded during the first phase.

In one embodiment, the elastic component or material recovers partially during the second phase by about 15 to 55%, preferably by about 20 to 50%, more preferably by about 25 to 45%, optionally by about 15 to 30% or 20 to 25%, optionally by about 40 to 55 or 45 to 50% of the total length to which the elastic component or material had been expanded during the first phase.

In one embodiment of the elastic component or material, relaxation, preferably the second phase, more preferably the second and third phases is/are self-initiated, preferably is/are initiated autonomously or spontaneously in the absence of an external stimulus.

In one embodiment, the elastic material or component has a delayed relaxation behaviour, preferably a delayed continuous relaxation behaviour.

In a sixth aspect, the invention provides an elastic fibre, filament, thread, or yarn comprising or consisting of an elastic component or material according to the invention (cf. fifth aspect).

In one embodiment, the elastic fibre, filament, thread, or yarn comprises or consists of a polyurethane (PU) polymer containing N-diol according to the invention (cf. eighth or ninth aspect).

In one embodiment, the elastic fibre, filament, thread, or yarn consists of the elastic component or material, or the PU polymer (e.g., in terms of a "naked" thread or yarn).

In one embodiment, the elastic thread or yarn comprises or consists of a core portion and/or a cover portion (e.g., a coating) comprising or consisting of the elastic component or material, or the PU polymer.

In one embodiment, the elastic thread or yarn comprises or consists of a core thread or yarn, and a cover thread or yarn wound around the core thread and yarn, respectively, the core thread or yarn and/or the wound core thread or yarn comprising or consisting of the elastic component or material, or the PU polymer.

In one embodiment, the elastic fibre, filament, thread, or yarn has been processed to a textile or fabric, preferably a compressive base fabric, more preferably according to the invention.

In one embodiment of the elastic fibre, filament, thread, or yarn, the textile or fabric is a knitted fabric, an interlaced fabric, a woven fabric, or a felt.

In a seventh aspect, the invention provides a compressive base fabric, preferably a compressive base knitted fabric, comprising or consisting of an elastic component or material according to the invention (cf. fifth aspect).

In one embodiment, the compressive base fabric comprises or consists of a polyurethane (PU) polymer containing N-diol according to the invention (cf. eighth or ninth aspect).

In one embodiment, the compressive base fabric comprises or consists of a base thread and a weft thread, the latter being drawn through, inserted over-and-under, the length of the base thread.

In one embodiment of the compressive base fabric, the base thread and/or the weft thread, and optionally at least one additional thread, e.g., a filler thread, comprises or consists of the elastic component or material, or the PU polymer.

In one embodiment, the compressive base fabric is a flat knitted fabric or a circular knitted fabric.

In an eighth aspect, the invention provides a polyurethane (PU) polymer having a delayed continuous relaxation behaviour, wherein relaxation is self-initiated, preferably is initiated autonomously or spontaneously in the absence of an external stimulus.

In one embodiment, the PU polymer additionally has features or combinations thereof as defined in the ninth aspect.

In a ninth aspect, the invention provides a polyurethane (PU) polymer containing N-diol.

In one embodiment, the PU polymer comprises at least one N-diol monomer component, preferably two or more, more preferably several or a multitude of N-diol monomer components.

In one embodiment, the PU polymer is a non-quaternised PU polymer (PU-N). This is a preferred embodiment.

In one embodiment, the PU polymer is a quaternised PU polymer (PU-N+).

In one embodiment, the PU polymer is a quaternised PU ionomer (PU-N+).

In one embodiment, the quaternised PU polymer or ionomer is derived from a non-quaternised PU polymer.

In one embodiment, the PU polymer is capable of being actively expanded and of relaxation upon release.

In one embodiment, the PU polymer is capable of passing through a relaxation process comprising or consisting of an immediate relaxation phase and a subsequent successive compression phase.

In one embodiment, the PU polymer is capable of passing through a first phase during which the material is expanded, a second phase during which the material relaxes without recovering or without completely recovering its original shape or with only partially recovering its original shape, and a third phase during which the PU polymer recovers its original shape, or virtually recovers or nearly completely recovers its original shape, preferably successively recovers its original shape, more preferably recovers its original shape with successive deceleration.

In one embodiment, the PU polymer recovers partially during the second phase by about 15 to 80%, more preferably by about 20 to 75%, optionally by about 15 to 30% or 20 to 25%, optionally by about 65 to 80 or 70 to 75% of the total length to which the PU polymer had been expanded during the first phase.

In one embodiment, the PU polymer recovers partially during the second phase by about 15 to 55%, preferably by about 20 to 50%, more preferably by about 25 to 45%, optionally by about 15 to 30% or 20 to 25%, optionally by about 40 to 55 or 45 to 50% of the total length to which the PU polymer had been expanded during the first phase.

In one embodiment of the PU polymer, relaxation, preferably the second phase, more preferably the second and third phases is/are self-initiated, preferably is/are initiated autonomously or spontaneously in the absence of an external stimulus.

In one embodiment of the PU polymer, relaxation is self-initiated or initiated without the impact of an external stimulus.

In one embodiment of the PU polymer, relaxation is self-initiated immediately upon release.

In one embodiment of the PU polymer, relaxation is self-initiated at room temperature.

In one embodiment, the PU polymer shows a delayed relaxation behaviour, preferably a delayed continuous relaxation behaviour, more preferably a relaxation behaviour which is delayed as compared to that of a PU polymer not containing N-diol.

In one embodiment of the PU polymer, the delayed relaxation behaviour is delayed in respect of duration of the immediate relaxation phase and/or successive compression phase.

In one embodiment of the PU polymer, the delayed relaxation behaviour is delayed in respect of the relative amount of relaxation achieved during the immediate relaxation phase and/or successive compression phase.

In one embodiment of the PU polymer, the delayed relaxation behaviour is delayed in respect of duration of the whole relaxation process.

In one embodiment of the PU polymer, the delayed relaxation behaviour is not delayed in respect of the initiation of relaxation.

In one embodiment, the PU polymer does not show a shape memory to the effect that shape recovery is initiated through the impact of an external stimulus.

In one embodiment, the quaternised PU polymer or ionomer comprises at least one ionic group, preferably two or more, more preferably several or a multitude of ionic groups.

In one embodiment, the quaternised PU polymer or ionomer comprises up to about 15%, preferably between about 1, 2, or 3 and 10%, more preferably between about 4 and 10%, even more preferably between about 3 and 7%, or between about 7 and 11%, even more preferably between about 4 and 6%, or between about 8 and 10%, most preferably about 5%, or about 9% of ionic groups, related to the total moles of the PU polymer.

In one embodiment of the quaternised PU polymer or ionomer, the ionic group is a quaternised N-containing group or a quaternary amino group, preferably a quaternised amino alkyl group. Optionally, the quaternised amino alkyl group is the only type of ionic group.

In one embodiment of the quaternised PU polymer or ionomer, the quaternised amino alkyl group contains alkyl groups of different lengths. Preferably, the quaternised amino alkyl group contains alkyl groups selected from the group consisting of methyl, ethyl, propyl, butyl, pentyl, hexyl, heptyl, and octyl groups. More preferably, the quaternised amino alkyl group contains a butyl group. Most preferably, the quaternised amino alkyl group contains one butyl group and two methyl groups ($-N^+-(CH_3)_2(CH_2-CH_2-CH_2-CH_3)$).

In one embodiment of the quaternized PU polymer or ionomer, the quaternised amino alkyl group is part of the N-diol monomer component.

In one embodiment, the PU polymer comprises or consists of at least one molecular unit, preferably two or more molecular units, more preferably several or a multitude of molecular units, consisting of a diol monomer component and an isocyanate monomer component.

In one embodiment of the PU polymer, the diol monomer component and the isocyanate monomer component are joined by a urethane link.

In one embodiment of the PU polymer, a diol monomer (which the diol monomer component is derived from) is selected from the group consisting of a N-diol, a 1,4-butanediol (BD) and a poly(tetrahydrofuran) (P(THF)).

In one embodiment, the PU polymer comprises or consists of a first molecular unit consisting of a N-diol monomer component and an isocyanate monomer component, a second molecular unit consisting of a 1,4-butanediol monomer component and an isocyanate monomer component, and a third molecular unit consisting of a P(THF) monomer component and an isocyanate component.

In one embodiment of the PU polymer, the first, second and third molecular units are joined by a urethane link, respectively.

In one embodiment of the PU polymer, the isocyanate monomer component in the third, second and third molecular units is identical or different. Preferably, the isocyanate monomer component is the same.

In one embodiment of the PU polymer, an isocyanate monomer (which the isocyanate monomer component is derived from) is methylenedi(phenylisocyanate) (MDI).

In one embodiment of the PU polymer, the N-diol is bis(2-hydroxyethyl)-3,3'-((2-(dimethylamino)ethypazanediyl)-dipropionate or N',N'-bis(3-(2-hydroxyethoxy)-3-oxopropyl)-N,N-dimethylethylendiamine.

In one embodiment of the PU polymer, a quaternised N-diol monomer component is produced by quaternization of a quaternisable N-diol monomer component.

In one embodiment of the PU polymer, a quaternisable N-diol monomer (which the quaternisable N-diol monomer component is derived from) is produced from 2-dimethylaminoethylamine (DMAE) and 2-hydroxyethylacrylate (HEA), preferably in a ratio of 1:2 (DMAE:HEA), more preferably in the presence of tetrahydrofuran (THF) at 45° C. for 24 hours.

In one embodiment of the PU polymer, the relative amounts of N-diol, P(THF) and BD monomer components are about 50:25:25%.

In one embodiment, the quaternised PU polymer or ionomer comprises an amount of quaternised N-containing groups of up to about 15%, preferably between about 1, 2, or 3 and 10%, more preferably between about 4 and 10%, even more preferably between about 3 and 7%, or between about 7 and 11%, even more preferably between about 4 and 6%, or between about 8 and 10%, most preferably about 5%, or about 9% of ionic groups, related to the total moles of the PU polymer.

In one embodiment, the PU polymer, preferably the non-quaternised PU polymer, has a glass transition temperature $T_g$ of between about 20 and 60° C., preferably of between about 30 and ° C., more preferably of between about 35 and 45° C., most preferably of about 40° C.

In one embodiment, the PU polymer, preferably the quaternised PU polymer, more preferably being quaternised at about 29%, has a glass transition temperature $T_g$ of about 40° C. and/or 70° C.

In one embodiment, said glass transition temperature is measured by dynamic-mechanical thermo-analysis (DMTA).

In one embodiment, the PU polymer, preferably the non-quaternised PU polymer, has a degradation temperature of between about 150 and 200° C., preferably between about 170 and 195° C., more preferably between about 180 and 190° C., most preferably of about 185° C.

In one embodiment, the PU polymer, preferably the non-quaternised PU polymer, has as fracture strain of between about 1,300 and 1,450 dL [%], more preferably between about 1,350 and 1,400 dL [%], more preferably between about 1,380 and 1,395 dL [%], most preferably of about 1,388 dL [%].

In one embodiment, the non-quaternised PU polymer is blended with at least one, two or more, or several quaternised PU polymers or ionomers.

In one embodiment, the quaternised PU polymer or ionomer is blended with at least one, two or more, or several non-quaternised PU polymers.

In one embodiment, the non-quaternised PU polymer and/or quaternised PU polymer or ionomer is blended with an elastane.

In one embodiment, the PU polymer is fibre or filament forming, preferably is fibre forming.

In one embodiment, the PU polymer forms or has been processed to a thread or yarn.

In one embodiment, the PU polymer has been processed to a textile or fabric, preferably a compressive fabric, optionally a compressive base fabric.

In a tenth aspect, the invention provides a blend comprising or consisting of:
(a) a non-quaternised polyurethane (PU) polymer containing N-diol (PU-N);
and/or
(b) a quaternised polyurethane (PU) polymer or ionomer containing quaternised N-diol (PU-N+);
and
(c) elastane.

In one embodiment, the blend comprises or consists of between about 5 and 40% (by weight) non-quaternised PU polymer or quaternised PU polymer or ionomer, and between about 60 and 95% (by weight) elastane.

In one embodiment, the blend comprises or consists of between about 10 and 30% (by weight) non-quaternised PU polymer or quaternised PU polymer or ionomer, and between about 70 and 90% (by weight) elastane.

In one embodiment, the blend consists of about 30% (by weight) non-quaternised PU polymer or quaternised PU polymer or ionomer, and 70% (by weight) elastane.

In one embodiment, and in a preferred embodiment, the blend consists of about 10% (by weight) non-quaternised PU polymer or quaternised PU polymer or ionomer, and 90% (by weight) elastane. The advantage of this embodiment is that the major amount of elastic polymer in the blend is commercially available and comparatively inexpensive elastane.

In one embodiment, an in a preferred embodiment, the blend comprises or consists of a non-quaternised PU polymer and elastane. The advantage of this embodiment is that the process step of quaternization can be avoided.

In one embodiment, the blend comprises or consists of at least one, two or more, or several non-quaternised PU polymers and elastane.

In one embodiment, the blend is fibre or filament forming, preferably is fibre forming.

In one embodiment, the blend forms or has been processed to a thread or yarn.

In one embodiment, the blend has been processed to a textile or fabric, preferably a compressive fabric, optionally a compressive base fabric.

In one embodiment of the blend, the non-quaternised PU polymer and/or the quaterised PU ionomer is one according to the invention (cf. eighth or ninth aspect).

In one embodiment, the blend is capable of passing through a first phase during which the blend material is expanded, a second phase during which the blend material relaxes without recovering or without completely recovering its original shape or with only partially recovering its original shape, and a third phase during which the blend material recovers its original shape, or virtually recovers or nearly completely recovers its original shape, preferably successively recovers its original shape, more preferably recovers its original shape with successive deceleration.

In one embodiment, the blend recovers partially during the second phase by about 15 to 80%, more preferably by about 20 to 75%, optionally by about 15 to 30% or 20 to 25%, optionally by about 65 to 80 or 70 to 75% of the total length to which the blend material had been expanded during the first phase.

In one embodiment, the blend recovers partially during the second phase by about 40 to 80%, preferably by about 50 to 75%, optionally by about 50 to 60% or 60 to 75% of the total length to which the blend material had been expanded during the first phase.

In one embodiment of the blend, relaxation, preferably the second phase, more preferably the second and third phases is/are self-initiated, preferably is/are initiated autonomously or spontaneously in the absence of an external stimulus.

In an eleventh aspect, the invention provides uses of an elastic component or material (cf. fifth aspect), an elastic fibre, filament, thread, or yarn (cf. sixth aspect), a compressive base fabric (cf. seventh aspect), a polyurethane (PU) polymer containing N-diol (cf. eighth or ninth aspect), or a blend (cf. tenth aspect) according to the invention in a compression product, preferably a medical compression product, or in a process for producing such a product.

In a twelfth aspect, the invention provides uses of a polyurethane (PU) polymer containing N-diol according to the invention (cf. eighth or ninth aspect) in a process for producing a compression product, an elastic component or material, an elastic fibre, filament, thread, or yarn, or a compressive base fabric, preferably according to the invention.

In a thirteenth aspect, the invention provides a use of a blend according to the invention (cf tenth aspect) in a process for producing a compression product, an elastic component or material, an elastic fibre, filament, thread, or yarn, or a compressive base fabric, preferably according to the invention.

In a fourteenth aspect, the invention provides a process for producing a polyurethane (PU) polymer containing N-diol comprising the steps of:
(i) Preparation of a quaternisable N-diol;
(ii) Preparation of a PU polymer containing a quaternisable N-diol as produced in step (i);
and, optionally,
(iii) Quaternization of the PU polymer produced in step (ii).

In one embodiment of the process, the PU polymer is one according to the invention.

In one embodiment, in step (ii) of the process, the quaternizable N-diol monomer and a 1,4-butanediol is provided first, and a poly(tetrahydrofuran) is added subsequently. This embodiment is preferred.

In one embodiment, in step (ii) of the process, the quaternizable N-diol monomer and a poly(tetrahydrofuran) is provided first, and a 1,4-butanediol is added subsequently.

In a fifteenth aspect, the invention provides a polyurethane (PU) polymer containing N-diol produced in accordance with a process of the invention.

Finally, the invention considers individual features or combinations thereof, as described above in respect of embodiments of a certain aspect, to be similarly realisable in embodiments under another described aspect. Such embodiments are directly and unambiguously derivable from the whole content of the application, and the skilled person will understand that such embodiments belong to the content of the application as filed.

DETAILED DESCRIPTION OF THE INVENTION

The invention provides, amongst others, compression products comprising a filament forming polyurethane (PU) polymer containing N-diol. This PU polymer may be present in the form of a non-quaternised PU polymer (PU-N) or a quaternised PU polymer (PU-N+), also referred to as PU ionomer, in which N-diol groups are quaternised. In either state, the PU polymer shows a delayed continuous relaxation behaviour at room temperature.

Such compression products can be expanded easily by hand without much physical effort on the part of the user (FIGS. 1A-1B, FIG. 2, phase (1)). Optionally, expansion can be supported or effected by the aid of an expansion means, for example a handbag or pocket compatible expansion means. Once the external expansion forces cease ("release"), the compression product starts relaxing and re-contracting in order to return to its original shape (FIGS. 1A-1B, phase (2)).

However, recovery of the original shape does not proceed linearly over time, but is more and more delayed. While relaxation proceeds more linearly at the beginning (FIGS. 1A-1B, phase (2)), the relaxation rate decelerates during the subsequent, e.g., five, minutes (FIGS. 1A-1B, phase (3)), and decelerates even more during the next 10 minutes and above, up to hours (FIGS. 1A-1B, phase (3)).

Thus, a compression product comprising the N-diol containing PU polymer of the invention provides the user with good time to put on or apply the product in a widened shape to a part of the body, e.g., a leg in case of a compression stocking (FIG. 2). There is no need to keep the product under external expansion forces during application, as it is the case with many conventional compression products. Then, the inventive product exerts a slowly increasing compression pressure on that part of the body which it was applied to. This is more pleasant to the user than a sudden pressure built-up, and this is also favourable from a medical perspective. For undressing or pulling off, the compression product is expanded again, e.g., in case of a compression stocking step-wise top-down, and is stripped off or removed.

In this way, a compression product of the invention is associated with increased comfort when being applied, which, in turn, positively affects the compliance of the user.

Notably, relaxation of a stretched PU polymer according to the invention is "self-initiated", i.e., starts autonomously or spontaneously or intrinsically, i.e., without being triggered by any external stimulus or activation source, as soon as the PU polymer is released. Accordingly, the compression products are applicable without the requirement of additional technical means or laborious and time-consuming operations.

In the end, use of the inventive compression products is not only comfortable and convenient, but also cost-effective.

The remarkable relaxation behaviour of the N-diol containing PU polymer of the invention, as compared to conventional elastic polymers, shall be illustrated with reference to FIGS. 3A-3B.

When a sample of elastane is stretched, e.g., with a fixed rate from an original length of 10 mm to a final length of 60 mm, and released (i.e., instant cease of stretching forces), elastane immediately recovers its original length (FIG. 3A). A conventional and commercially available PU polymer (i.e., not containing N-diol) recovers about 84% of its extended length immediately, but remains stretched by about 16% for a few days, i.e., does no recover its original length (FIG. 3B).

In contrast, as shown in FIGS. 16A-16D, the PU polymer of the invention, either non-quaternised or quaternised (with different degrees) shows a relaxation behaviour composed of an immediate relaxation phase (phase 2 in FIGS. 1A-1B) and relaxation phase of successive compression (phase 3 in FIGS. 1A-1B).

In other words, compared to elastane and conventional PU polymers, the PU polymer of the invention shows a still continuous, but delayed relaxation behaviour. Furthermore, as demonstrated by comparison with the conventional PU polymer, this delayed relaxation behaviour depends on the presence of N-diol.

Moreover, the delayed relaxation behaviour can be controlled by modifying the composition of the inventive PU polymer (in terms of monomer components, e.g., ratio of monomers), by quaternization, and by the degree of quaternization. For example, a low degree of quaternization (e.g., 9% or 5%) of the inventive PU polymer led to a faster relaxation as compared to that of the corresponding non-quaternised PU polymer, and to that of a PU-N+ polymer being quaternised at 29%.

Finally, the relaxation behaviour of the PU polymer of the invention can be further modified by admixture of elastane. The other way around, elastane can be provided with a delayed relaxation behaviour by admixture of the inventive PU polymer. Such blends with elastane, depending on their relative compositions, open up new possibilities of uses, for example in the field of in compression products.

Definitions

The terms "polyurethane (PU) polymer containing N-diol" or "N-diol containing polyurethane (PU) polymer", as used herein, includes:
(1) A "non-quaternised polyurethane (PU) polymer", i.e., a PU polymer containing N-diol, the amino group of which are not quaternised, but are tertiary amino groups. For simplification, "PU-N" is sometimes used.
(2) A "quaternised polyurethane (PU) polymer" or a "quaternised polyurethane (PU) ionomer" or a "polyurethane (PU) ionomer", i.e., a PU polymer containing N-diol, the amino groups of which are at least partially quaternised. For simplification, "PU-N+" is sometimes used.

The term "quaternization", as used herein, relates to a chemical reaction in which a nitrogen atom (of a tertiary amino group) is gone from having three bindings to four bindings through alkylation, producing a 4-fold substituted derivative (i.e., a quaternary ammonium compound).

The resulting compound may be referred to as being "quaternised".

The "degree of quaternization", as used herein, denotes the proportion of quaternary aminoalkyl groups relative to the total number of aminoalkyl groups in a given compound.

An "ionomer" is defined as an ion-containing polymer with low mol % of ionic groups along the polymer backbone chains or as pendant groups. The amounts of ionic groups distinguish an ionomer from a polyelectrolyte. Usually, ionomers are defined as containing an ion-content of up to around 15 mol %.

Ionomers have been described in the prior art, e.g., ethylene/carboxylic acid ionomer fibres for gas filters (U.S. Pat. No. 5,882,519), or polyurethane ionomers for films and laminates (U.S. Pat. No. 4,956,438). Further information can also be found in, e.g., Dieterich et al. (1970), Angew. Chem. internat. Edit. 9: 40-50; Kim et al. (1998), Polymer 39: 2803-2808; Zhu et al. (2008), Polym. Adv. Technol. 19: 1745-1753.

The term "elasticity" (or "elastic") defines the ability of a material to resist a distorting influence or deforming force and to return to its original size and shape when that influence or force is removed. For rubbers or other polymers, elasticity is caused by stretching of polymer chains when forces are applied.

The term "expansion", as used herein, includes stretching, widening, extension, elongation, distortion, deformation, or other non-destructive changes in shape of an elastic material. The term "expansion" is used more in relation to the deformation of a compression product or fabric, while the term "stretching" or "elongation" is used more in relation to an elastic polymer or fibre.

The term "compression product", as used herein in some embodiments, refers to a product that, when worn by a patient, exerts a compression on the wearer. Typically, it exerts such compression in those body regions of the patient that come into contact with the compression product while it is being worn. Typically, also, a compression product is not a ridged product but is capable of being deformed, stretched, expanded, etc. whilst retaining a tendency or propensity to return to its original shape. The term "relaxation", as used herein, refers to the behaviour and condition of a previously expanded elastic material after being released.

The term "release", as used herein, refers to the cease of expansion forces or to the moment when such forces cease or stop.

The "first phase" of a relaxation process, as used herein, refers to an "expansion phase", "stretching phase" or "active elongation phase". During this phase, expansion or stretching forces are increasingly applied to the elastic material (or PU polymer or blend). In order to maintain the amended shape or extended length, expansion or stretching forces need to be applied further on.

The "second phase" refers to a phase of immediate relaxation or "immediate relaxation phase". During this phase, the original shape or length of the elastic material (or PU polymer or blend) is only partially recovered. Relaxation proceeds more linearly and thus this phase may also be referred to as a "linear phase" or "stabile phase". This second phase is self-initiated once the expansion or stretching forces cease, i.e., in the absence of an external stimulus.

The "third phase" refers to a phase of successive relaxation or "successive relaxation phase". During this phase, the elastic material (or PU polymer or blend) successively or gradually recovers its original shape or length. Notably, the successive or gradual recovery is featured by deceleration or increased retardation or growing delay or progressive slow-down. In other words, the third phase may be subdivided in several sub-phases during which relaxation proceeds with different velocities (for example at least a first sub-phase lasting, e.g., about 5 minutes and a second sub-phase lasting from, e.g., about 10 minutes up to 6 hours). The third phase is also self-initiated and continues the second phase. In particular in the context of a compression product, this phase is also referred to as "successive compression phase".

In the context of the third phase, the wording "recovers its original shape", "virtually recovers its original shape", or "nearly completely recovers its original shape" means that the elastic material (or PU polymer or blend) recovers by at least from about 85 to 100%, preferably by from about 90 to 100%, more preferably by from about 95 to 100%, even more preferably by 100±5%, and most preferably by about 100% of the shape or total length to which the elastic material had been expanded during the first phase. Alternatively, said wording means that the elastic material recovers to at least from about 100 to 150%, preferably to from about 100 to 125%, more preferably to from about 100 to 110%, even more preferably to 100±5%, and most preferably to about 100% of its original shape or length, i.e., its shape or length prior to expansion.

The term "delayed relaxation behaviour" or "delayed continuous relaxation behaviour", as used herein, means that the relaxation behaviour is delayed in time as compared to a reference relaxation behaviour. Herein, the refence material may be any elastic polymer or a PU polymer not containing N-diol. The delay may relate to the duration of one or more phases of the relaxation process, or to the duration of the whole relaxation process.

The term "continuous" in connection with a "delayed continuous relaxation behaviour" means that the relaxation process proceeds continuously, either linearly or increasingly retarded, in any case without, e.g., temporary persistence of an intermediate shape.

The expression, as used herein, according to which "a monomer component is derived from" or "is based on" a specific compound means that the compound was used for preparing a polymer. Thus, the monomer component corresponds to the compound, but in a state in which the compound is bound within the polymer.

The term "about", as used herein along with numbers or data, intends to include deviations (±) which usually are to be considered in the respective technical field.

Abbreviations
BD 1,4-butanediol
DBTL dibutyltin dilaurate
DMAE 2-dimethylaminoethylamine
DMTA dynamic-mechanical thermoanalysis
GPC gel permeation chromatography
HEA 2-hydroxyethylacrylate
MDI methylene diisocyanate, 4,4'-diphenylmethanediisocyanate
PU polyurethane
PU-N polyurethane containing N-diol, non-quaternised
PU-N+ polyurethane containing quaternised N-diol, quaternized polyurethane
P(THF) poly(tetrahydrofuran), poly(tetramethyleneetherglycol) 1000
$T_g$ glass transition temperature
TGA thelinogravimetric analysis
THF tetrahydrofuran

BRIEF DESCRIPTION OF THE FIGURES

Below, the invention will be illustrated further by means of the following examples taking into account the accompanying figures, in which.

E' [Pa]=dynamic modulus, tan δ=mechanic loss factor, $T_g$=glass transition temperature.

Figure 14A:
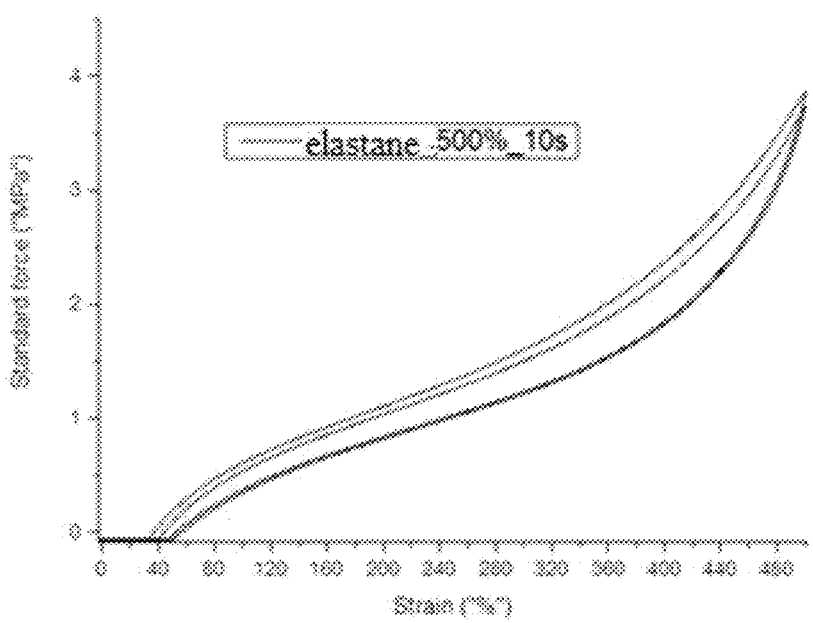
Figure 14B:
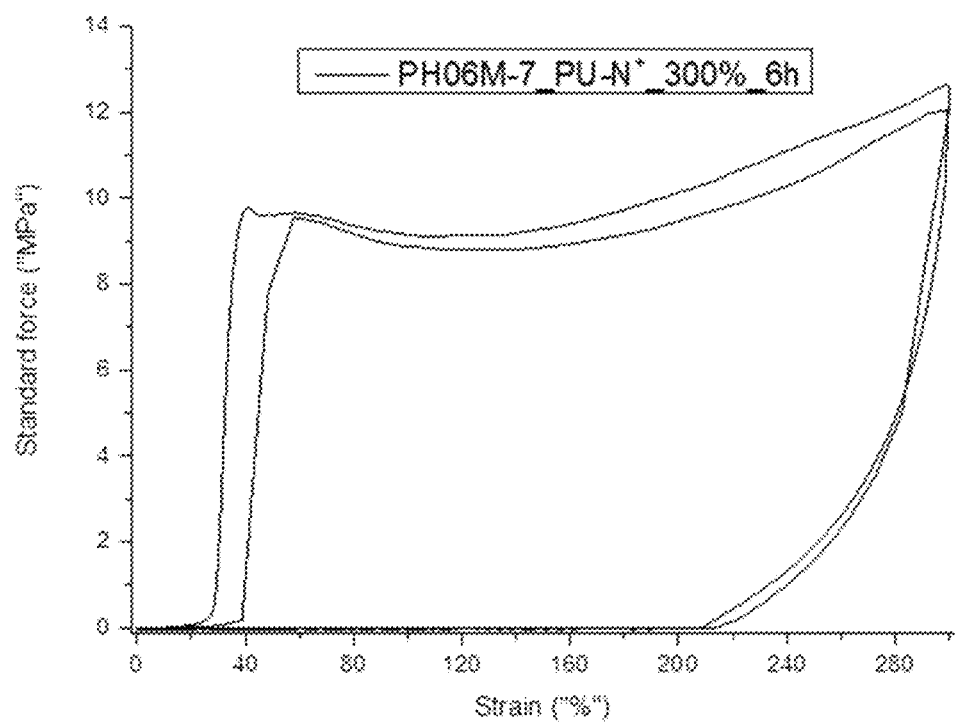

FIGS. 14A-14B show results from stress-strain tests with elastane (14A) or PU-N+(14B).

Figure 15A:
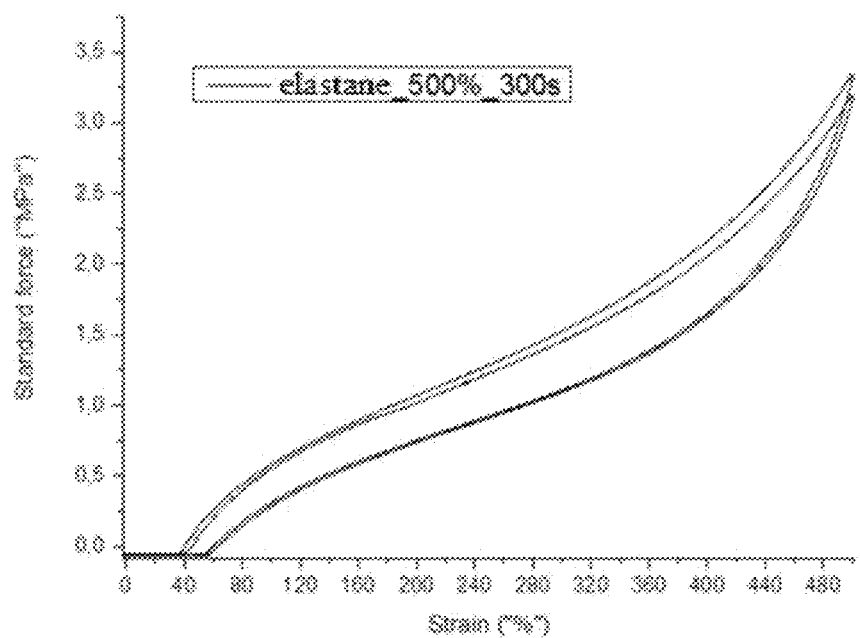
Figure 15B:
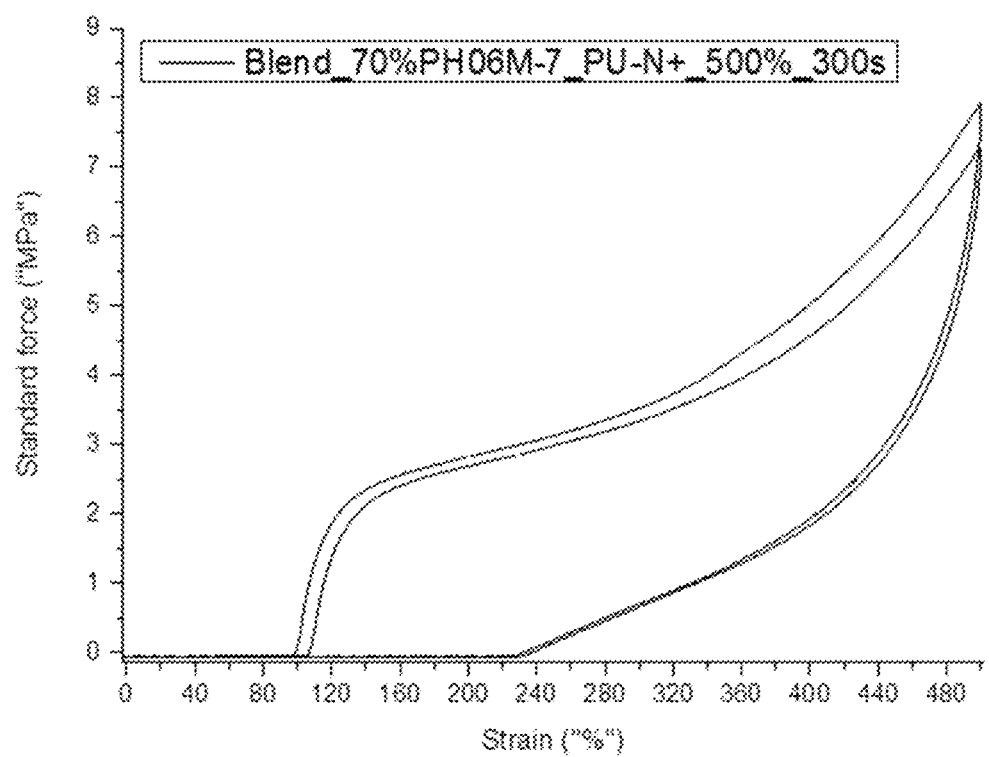

FIGS. 15A-15B show results from stress-strain tests with elastane (15A) or PU-N+ blended with 30% elastane (15B).

FIGS. 16A-16D illustrate the relaxation behaviour of PU-N (16A) and PU-N+(16B-16D) having a quaternization degree of 29% (16B), 9% (16C), or 5% (16D).

Figure 17:
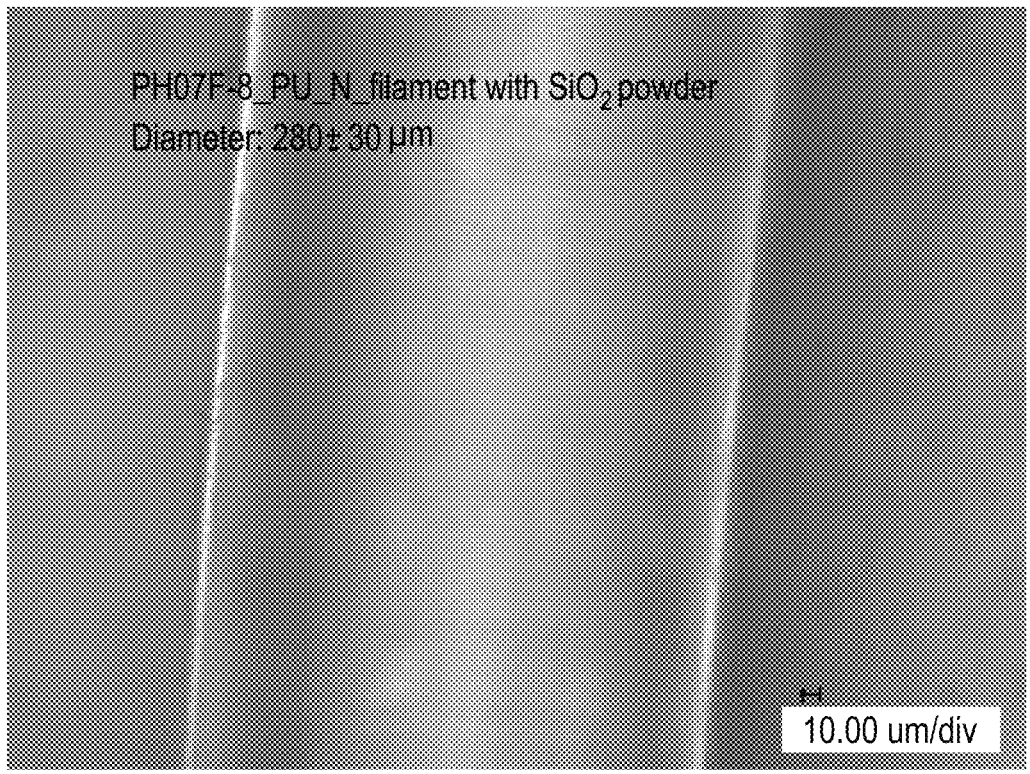

FIG. 17 shows a microscopic image (500× magnification) of α PU-N+(i. e. quarternized polymer) spun into a filament that has been powdered with a suitable powder, e. g. $SiO_2$, to prevent sticking to the filament.

Figure 18:
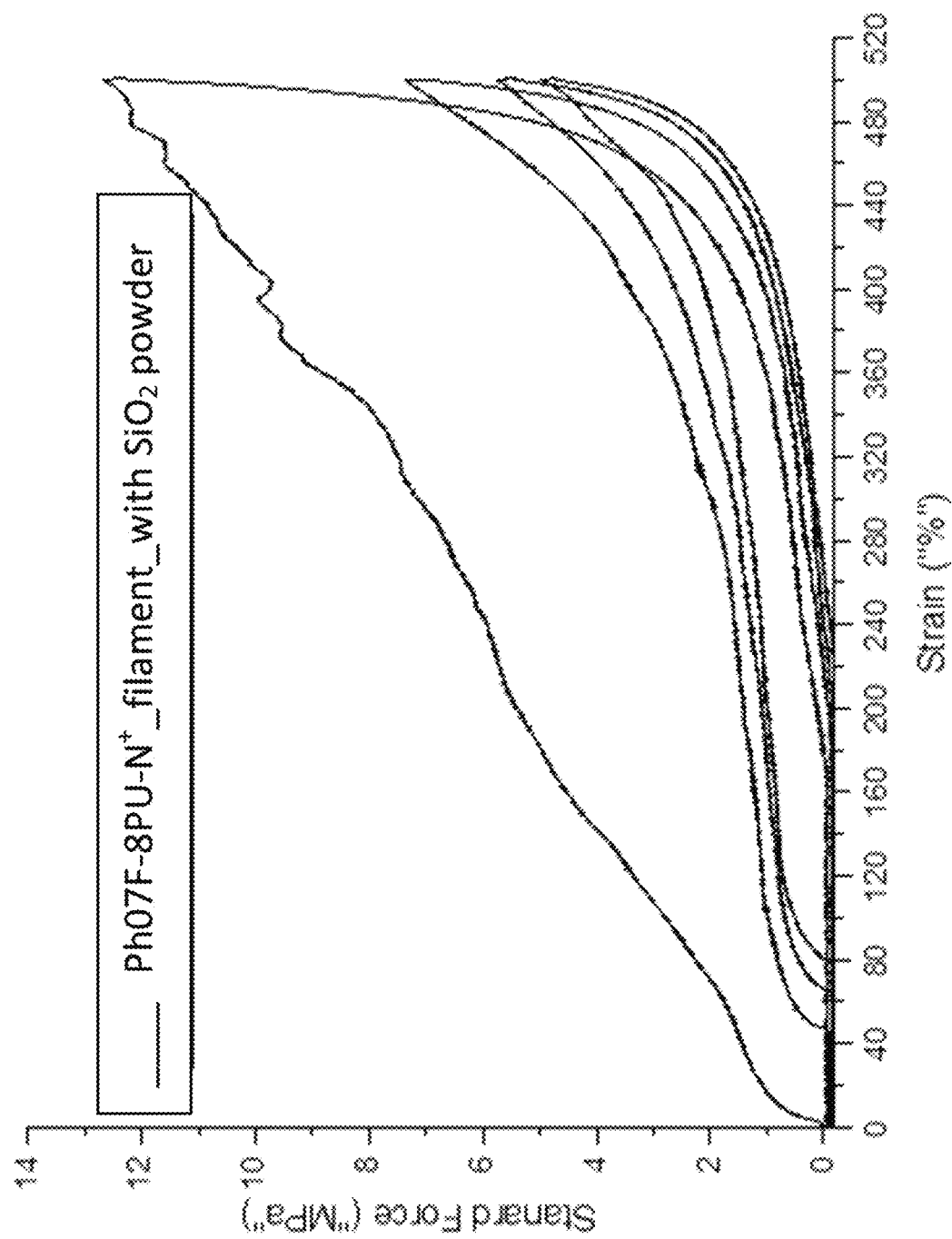

FIG. 18 shows results from stress-strain-tests with filaments of PU-N+.

Figure 19:
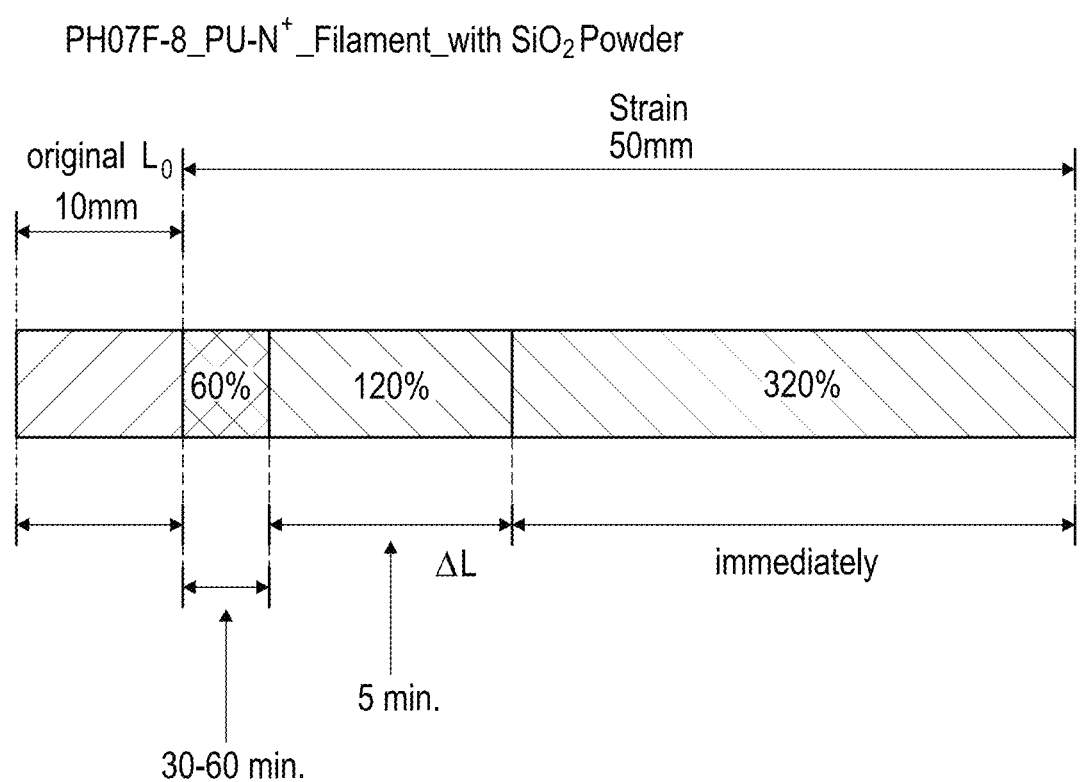

FIG. 19 illustrates the relaxation behaviour of PU-N+ filaments

EXAMPLES

Briefly, Examples 1 and 2 relate to the preparation of N-diol containing PU polymer, Example 5 relates to the preparation of corresponding quaternised PU polymer. Generally, the preparation processes described, i.e., developed on a laboratory scale, are suitable for being processed to industrial-scale.

Examples 3 and 4 describe the characterisation of N-diol containing PU polymers in regard to molecular mass and decomposition temperature; Example 6 describes the characterisation of quaternised PU polymers.

Examples 7 and 8 make comparisons of N-diol containing PU polymers and elastane in regard to glass transition temperature ($T_g$) and tensile strength (modulus of elasticity, fracture strain).

Example 9 relates to blends of N-diol containing PU polymers and elastane, and describes their tensile strengths.

Examples 10 and 11 describe the relaxation behaviour of N-diol-containing PU polymers and of blends with elastane, respectively.

In Table 16, characterising features of exemplary polymer samples described and discussed in some of the examples below, are summarized.

Example 1: Preparation of N-Diol

Chemicals

N,N-Dimethylethylendiamine (DMEA): CAS: 108-00-9, Acros, distilled before use; 2-hydroxyethylacrylate (HEA): CAS: 818-61-1, TCI, >95%; THF: technical grade, dried and distilled before use; $Et_2O$: technical grade, dried and distilled before use.

| Chemical | M [g·mol⁻¹] | n [mol] | M [g] | D [g·cm⁻³] | V [ml] | eq. |
|---|---|---|---|---|---|---|
| DMEA | 88.15 | 0.594 | 48.42 | 0.807 | 60 | 1 |
| HEA | 116.12 | 1.099 | 127.57 | 1.106 | 115.3 | 2 |
| THF | 72.11 | 1.23 | 88.9 | 0.889 | 100 | 2.1 |

Procedure 115.3 ml (1.099 mol) HEA and 100 ml THF were taken in a 500 ml 3-neck-round-bottom flask under inert gas (argon) at room temperature (20±2° C.). 60 ml (0.594 mol) DMEA was added to this solution drop-wise. The mixture was stirred at 45° C. in an oil bath for 24 h. After this time, the solvent was removed and the left over (yellowish liquid) was extracted with $Et_2O$ (4×100 ml $Et_2O$, product is not soluble in $Et_2O$). The product was dried in vacuum at 50° C.

Yield: 132 g, 75%.

The product was characterised by 1H-NMR spectroscopy.

Figure 1A:
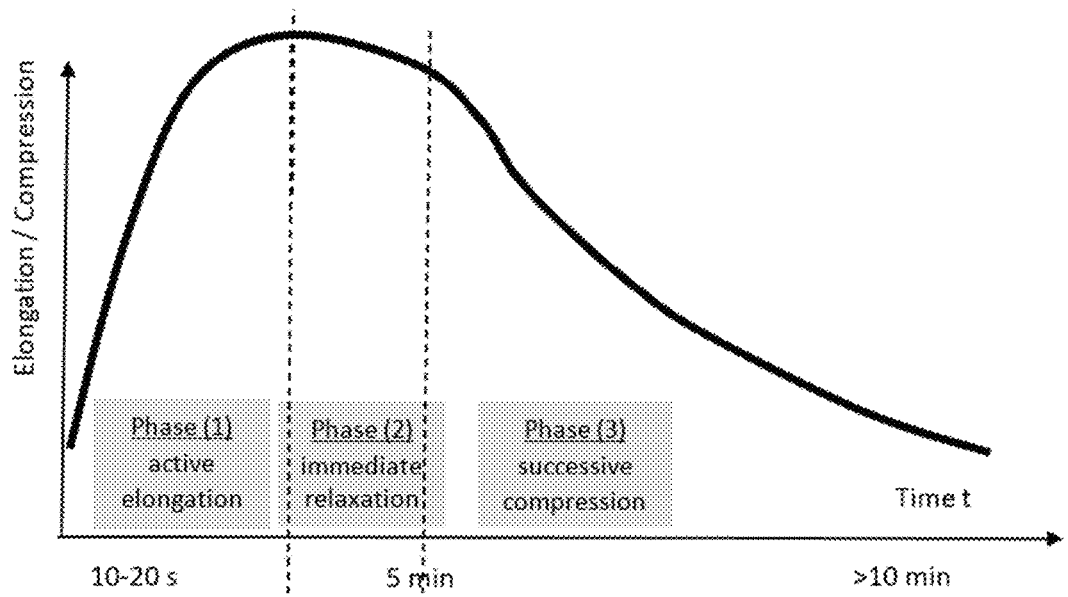
FIGS. 1A-1B show diagrams (1A) and (1B) illustrating a phase of active elongation (1), a phase of immediate relaxation (2), a phase of successive compression (3), which a polyurethane (PU) polymer containing N-diol (PU-N or PU-N+) passes through in the course of elongation—relaxation, and eventually recovery of original shape.
Figure 1B:
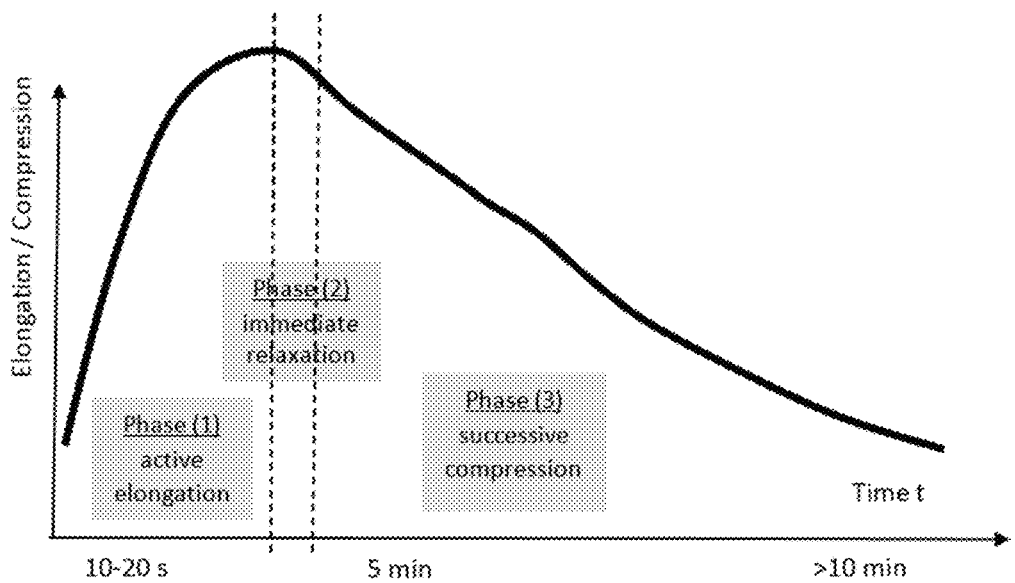
Figure 2:
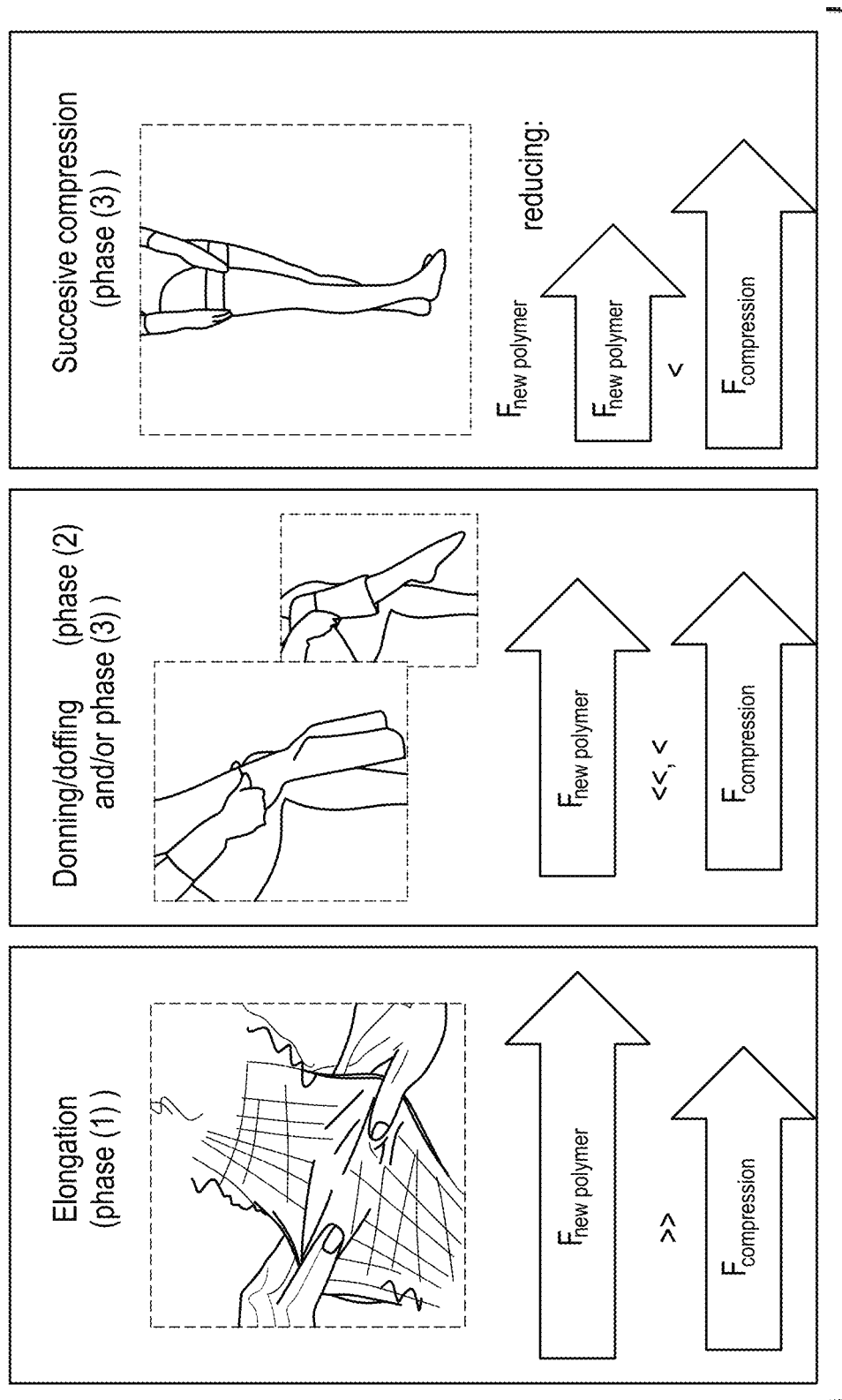
FIG. 2 shows phases (1) to (3) (see FIGS. 1A-1B) in relation to an application procedure by a user (here: donning/doffing a compression stocking).
Figure 3A:
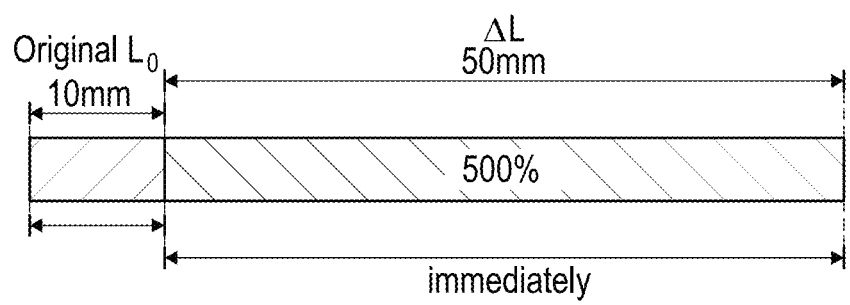
FIGS. 3A-3B illustrate the relaxation behaviour of (3A) elastane and (3B) a conventional polyurethane polymer not containing N-diol (50% P(THF), 50% BD).
Figure 3B:
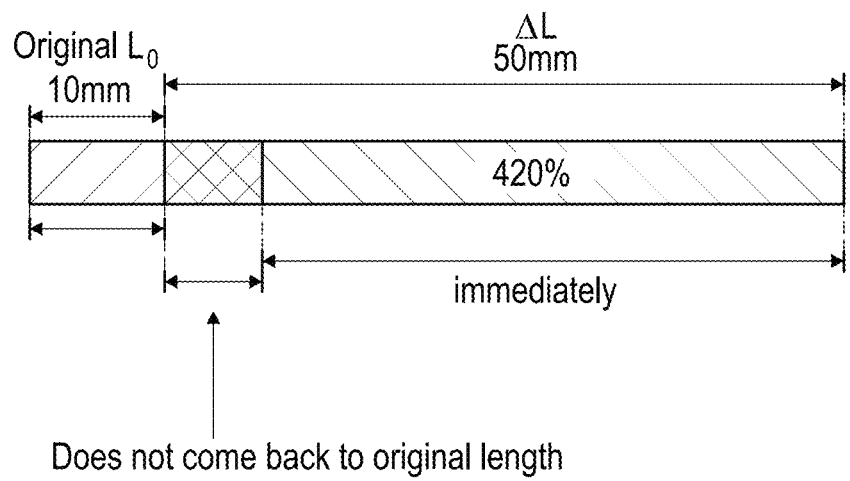
Figure 4:
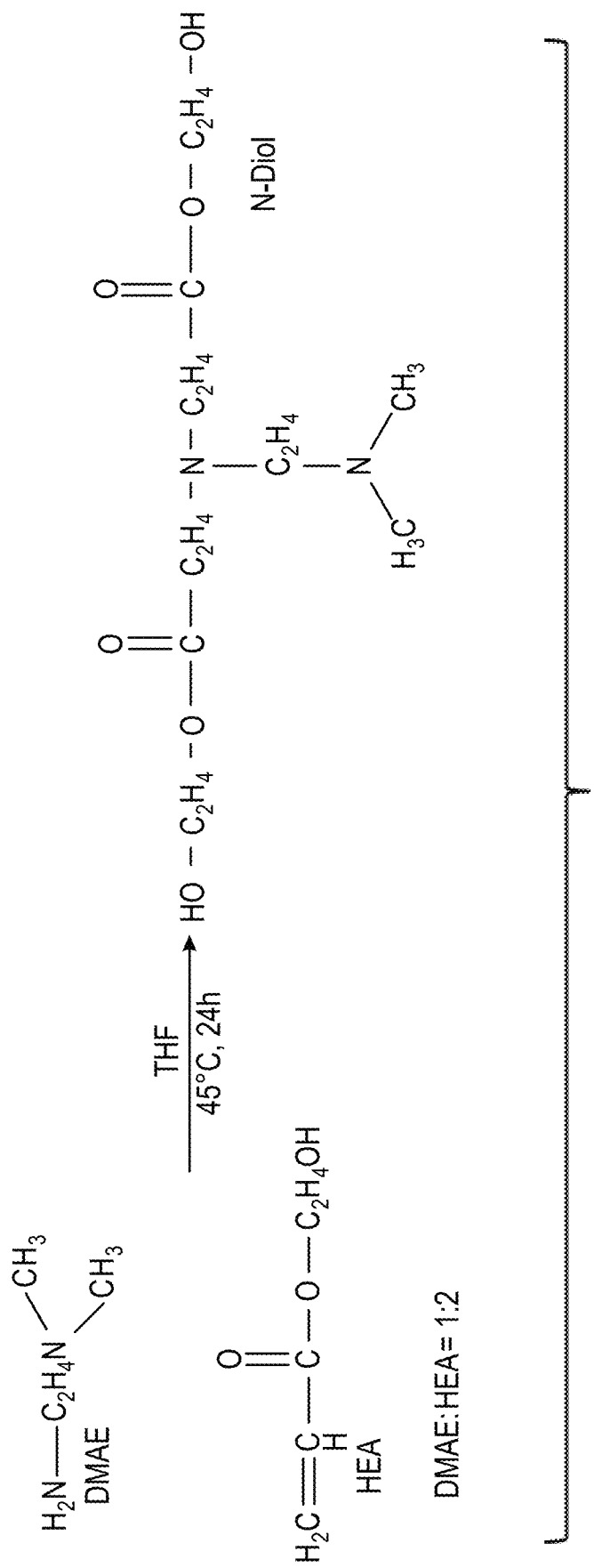
FIG. 4 shows a reaction scheme illustrating the chemical synthesis of a N-diol from 2-dimethylaminoethylamine (DMAE) and 2-hydroxyethylacrylate (HEA).

A reaction scheme is shown in FIG. 4.

Example 2: Preparation of Polyurethane (PU) Polymer Containing N-Diol (PU-N)

Chemicals 1,4-Butanediol (BD): CAS: 110-63-4, distilled before use; Poly(THF) 1000: CAS: 25190-60-1, $M_n$ (number average molar mass)=1,000 g/mol, Merck; 4,4'-diphenylmethanediisocyanate (MDI): CAS: 101-68-8, >97%, TCI; dibutyltin dilaurate (DBTL): CAS: 77-58-7, Sigma-Aldrich;

THF: technical grade, dried and distilled before use.

Reaction 1:

| Chemical | M [g·mol⁻¹] | n [mol] | M [g] | D [g·cm⁻³] | V [ml] | eq. |
|---|---|---|---|---|---|---|
| N-Diol (as synthesized in Example 1) | 320.19 | 0.00448 | 1.435 | | | 0.5 |
| Poly(THF) 1000 | 1,000 | 0.00896 | 8.96 | | | 1 |
| BD | 90.12 | 0.00448 | 0.404 | 1.02 | 0.396 | 0.5 |
| MDI | 250.25 | 0.01874 | 4.69 | 1.05 | | 2.08 |
| DBTL | 631.56 | 1.22·10⁻⁴ | 0.077 | 1.066 | 0.0726 | 0.5 wt % |
| THF | 72.11 | 0.247 | 17.78 | 0.889 | 20 | 27.5 |

Reaction 2:

| Chemical | M [g·mol⁻¹] | n [mol] | M [g] | D [g·cm⁻³] | V [ml] | eq. |
|---|---|---|---|---|---|---|
| Diol (PH16N-6) | 320.19 | 0.00896 | 2.87 | | | 1 |
| Poly(THF) 1000 | 1,000 | 0.00448 | 4.48 | | | 0.5 |
| BD | 90.12 | 0.00448 | 0.404 | 1.02 | 0.396 | 0.5 |
| MDI | 250.25 | 0.01874 | 4.69 | 1.05 | | 2.08 |
| DBTL | 631.56 | 0.985·10⁻⁴ | 0.06 | 1.066 | 0.0563 | 0.5 wt % |
| abs. THF | 72.11 | 0.247 | 17.78 | 0.889 | 20 | 27.5 |

Reaction 3:

| Chemical | M [g·mol⁻¹] | n [mol] | M [g] | D [g·cm⁻³] | V [ml] | eq. |
|---|---|---|---|---|---|---|
| Diol (PH16N-6) | 320.19 | 0.00448 | 1.435 | | | 0.5 |
| Poly(THF) 1000 | 1000 | 0.00448 | 4.48 | | | 0.5 |
| BD | 90.12 | 0.00896 | 0.808 | 1.02 | 0.792 | 1 |
| MDI | 250.25 | 0.01874 | 4.69 | 1.05 | | 2.08 |
| DBTL | 631.56 | 0.903·10⁻⁴ | 0.057 | 1.066 | 0.0535 | 0.5 wt % |
| abs. THF | 72.11 | 0.247 | 17.78 | 0.889 | 20 | 27.5 |

Procedure

MDI and DBTL were mixed with 20 ml dried THF in 100 ml nitrogen flask under argon. The solution was cooled in an ice bath. N-Diol and BD were added dropwise to this cooled solution within 10 min. After addition was finished, the mixture was stirred for 30 min at room temperature. After this, poly(THF) was added dropwise and stirred for further 1 h. Afterwards, the reaction contents were heated at 50° C. (oil bath temperature) for 2 h. Afterwards, the polymer formed was precipitated in MeOH and dried at 50° C. in vacuum. Yield: 89%.

Figure 5:
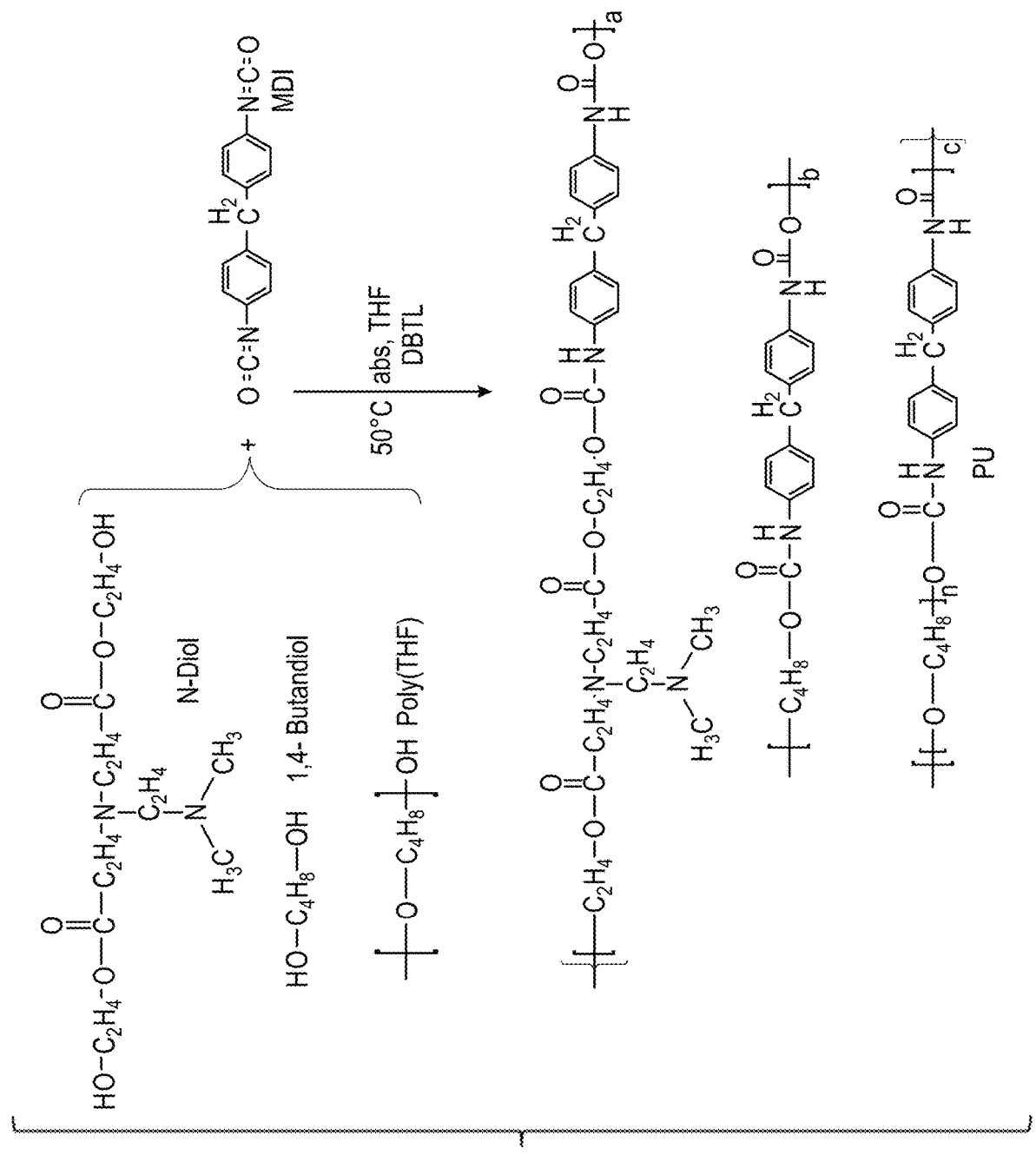
FIG. 5 shows a reaction scheme illustrating the chemical synthesis of PU-N from N-diol, 1,4-butanediol (BD), poly (tetrahydrofuran) (P(THF)), and methylene diisocyanate (MDI).

A reaction scheme is shown in FIG. 5.

Example 3: Comparison of Different Ratios of Monomers

PU-N synthesis as described in Example 2 was carried out based on ratios of monomers given in Table 1 below.

TABLE 1

| Sample | N-Diol/eq. | P(THF)/eq. | BD/eq. | MDI/eq. |
|---|---|---|---|---|
| PH18N-6 (Comp. sample) | 1 | 0 | 0 | 1.04 |
| PH21N-6 (Comp. sample) | 1 | 0 | 1 | 2.08 |
| PH15D-6 (Comp. sample) | 0 | 1 | 1 | 2.08 |
| PH23N-6 | 0.5 | 1 | 0.5 | 2.08 |
| PH24N-6 | 1 | 0.5 | 0.5 | 2.08 |
| PH18J-7 | 0.5 | 0.5 | 1 | 2.08 | eq. = equivalent

Figure 7:
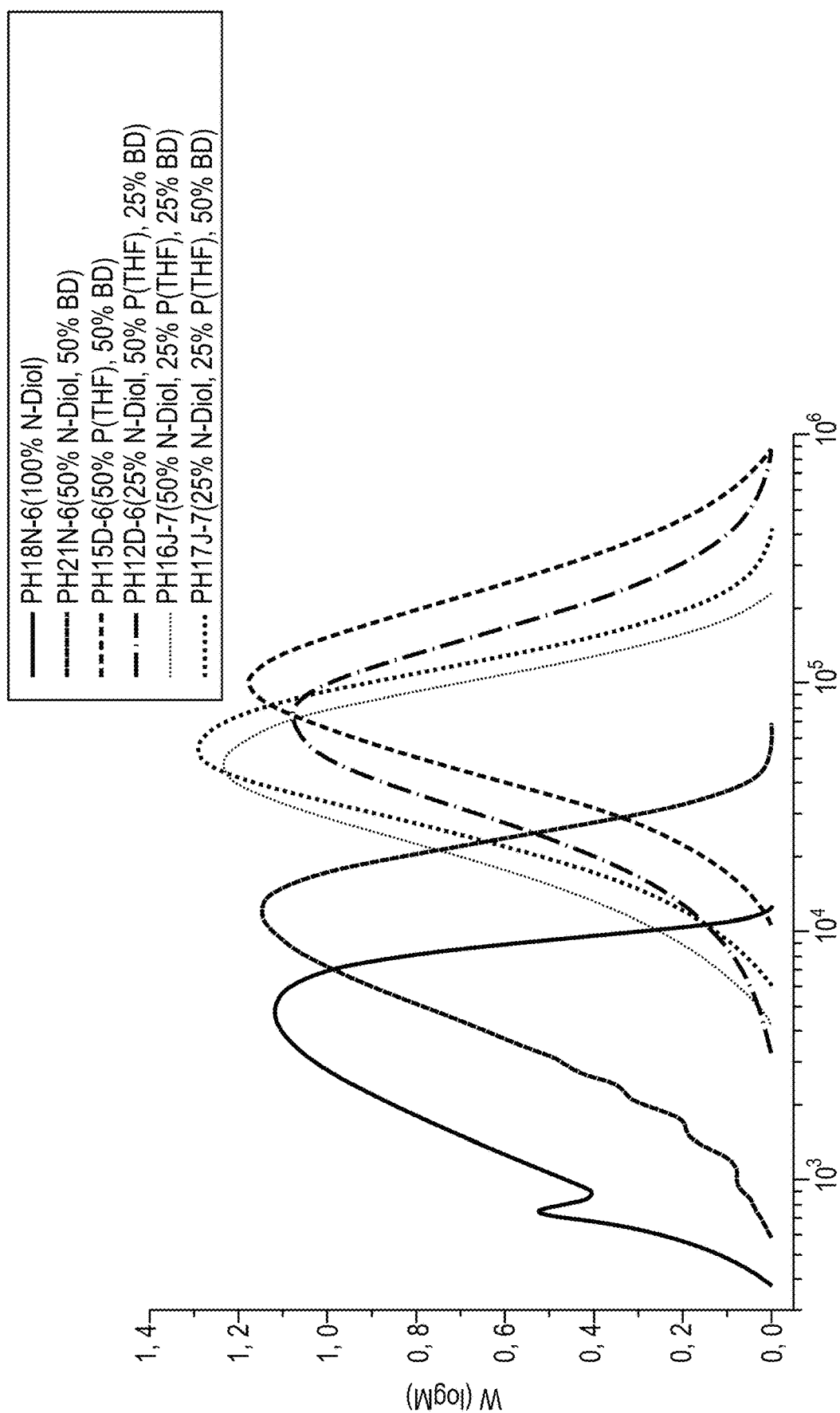
FIG. 7 shows the analysis by GPC (eluent: THF) of samples of PU-N+ composed of different ratios of monomers.
Figure 8:
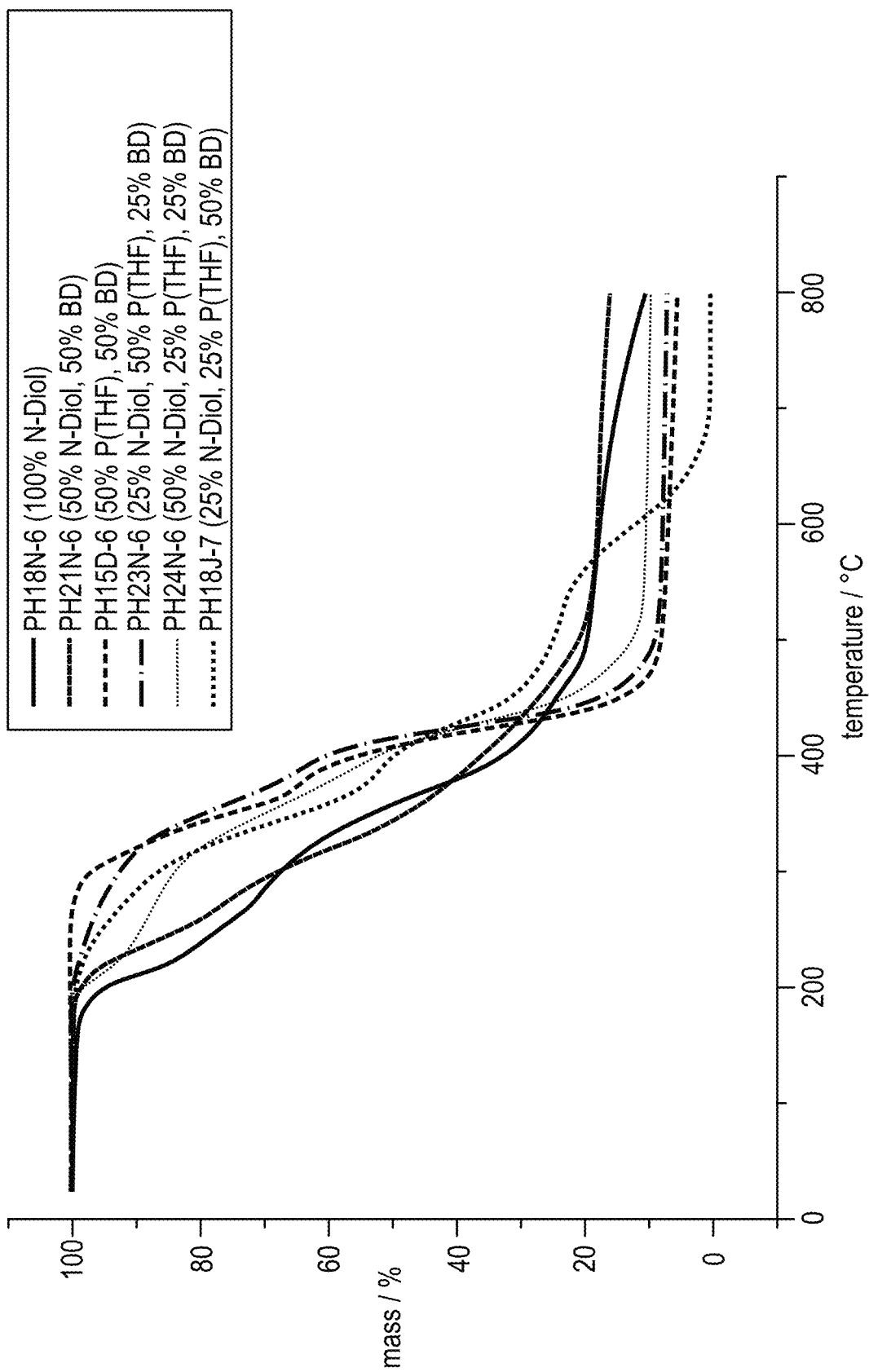
FIG. 8 shows the analysis by TGA (25-800° C., 10 K/min, $N_2$) of samples of PU-N+ composed of different ratios of monomers.

Samples containing the PU-N product were analysed by GPC (FIG. 7) and TGA (FIG. 8).

Gel permeation chromatography (GPC) was used for molar mass determination (instrument: Agilent Technologies 1200 Series/1260 Infinity; column 1: PSS SDV 5 µm 100000; column 2: PSS SDV 5 µm 10000; column 3: PSS SDV 5 µm 1000; column 4: PSS SDV 5 µm 100; detector 1: Waters 486 UV; detector 2: Techlab Shodex RI; eluent: THF; flow rate: 1.0 ml/min; column temperature: 40° C.; calibration standard: polystyrene).

Thermogravimetric analysis (TGA) was used to determine the thermal stability. A Netzsch TG 209 F1 Libra was used. Samples were heated from 25 to 800° C. in $Al_2O_3$-pans. Ca. 5-10 mg polymers were measured with a balance and put in a sample-pan. Whole measurement was done under air with a heating rate of 10° C./min. The temperature at which the weight loss started is mentioned as degradation temperature.

As shown in FIG. 7, the molecular mass of PU contained in comparison samples PH18N-6 (100% N-diol) and PH21N-6 (50% N-diol, 50% BD) turned out to be too low. The highest molecular mass was shown by comparison sample PH15D-6 (50% P(THF), 50% BD).

Amongst PU-N samples PH24N-6 (50% N-diol, 25% P(THF), 25% BD), PH23N-6 (25% N-diol, 50% P(THF), 25% BD), and PH18J-7 (25% N-diol, 25% P(THF), 50% BD), the molecular mass increased with the amount of P(THF) and BD.

The results to be seen from FIG. 7 are summarised in Table 2 below.

TABLE 2

| Sample | Mn [g/mol] | D |
|---|---|---|
| PH18N-6 | $3.3 \cdot 10^3$ | 1.4 |
| PH21N-6 | $5.7 \cdot 10^3$ | 1.9 |
| PH15D-6 | $7.5 \cdot 10^4$ | 1.8 |
| PH23N-6 | $2.3 \cdot 10^3$ | 2.1 |
| PH24N-6 | $1.6 \cdot 10^3$ | 2.2 |
| PH18J-7 | $3.1 \cdot 10^3$ | 2.0 |

Mn = molar mass;
D = molecular mass [Da]

As shown in FIG. 8, an increased amount of P(THF) or BD resulted in a higher decomposition temperature.

The results to be seen from FIG. 8 are summarised in Table 3 below.

TABLE 3

| Sample | 5% decomposed [° C.] |
|---|---|
| PH18N-6 | 199 |
| PH21N-6 | 219 |
| PH15D-6 | 307 |
| PH23N-6 | 278 |
| PH24N-6 | 213 |
| PH18J-7 | 246 |

Example 4: Comparison of Different Sequences of Addition of Monomers

PU-N synthesis as described in Example 2 was carried out by adding first N-diol+P(THF) and subsequently BD (option 1), or by adding first N-diol+BD and subsequently P(THF) (option 2).

Option 1: PH23N-6, PH24N-6, PH18J-7
  (i) MDI+DBTL in abs. THF, cooling down on ice
  (ii) Adding N-diol+P(THF) (in drops), stirring 30 min at room temperature (iii) Adding BD (in drops)
Option 2: PH12D-6, PH16J-7, PH17J-7
  (i) MDI+DBTL in abs. THF, cooling down on ice
  (ii) Adding N-diol+BD (in drops), stirring 30 min at room temperature
  (iii) Adding P(THF) (in drops)

The ratios of monomers were as given in Table 4 below.

TABLE 4

| Sample | N-Diol/eq. | P(THF)/eq. | BD/eq. | MDI/eq. |
|---|---|---|---|---|
| PH23N-6 PH12D-6 | 0.5 | 1 | 0.5 | 2.08 |
| PH24N-6 PH16J-7 | 1 | 0.5 | 0.5 | 2.08 |
| PH18J-7 PH17J-7 | 0.5 | 0.5 | 1 | 2.08 |

Figure 9:
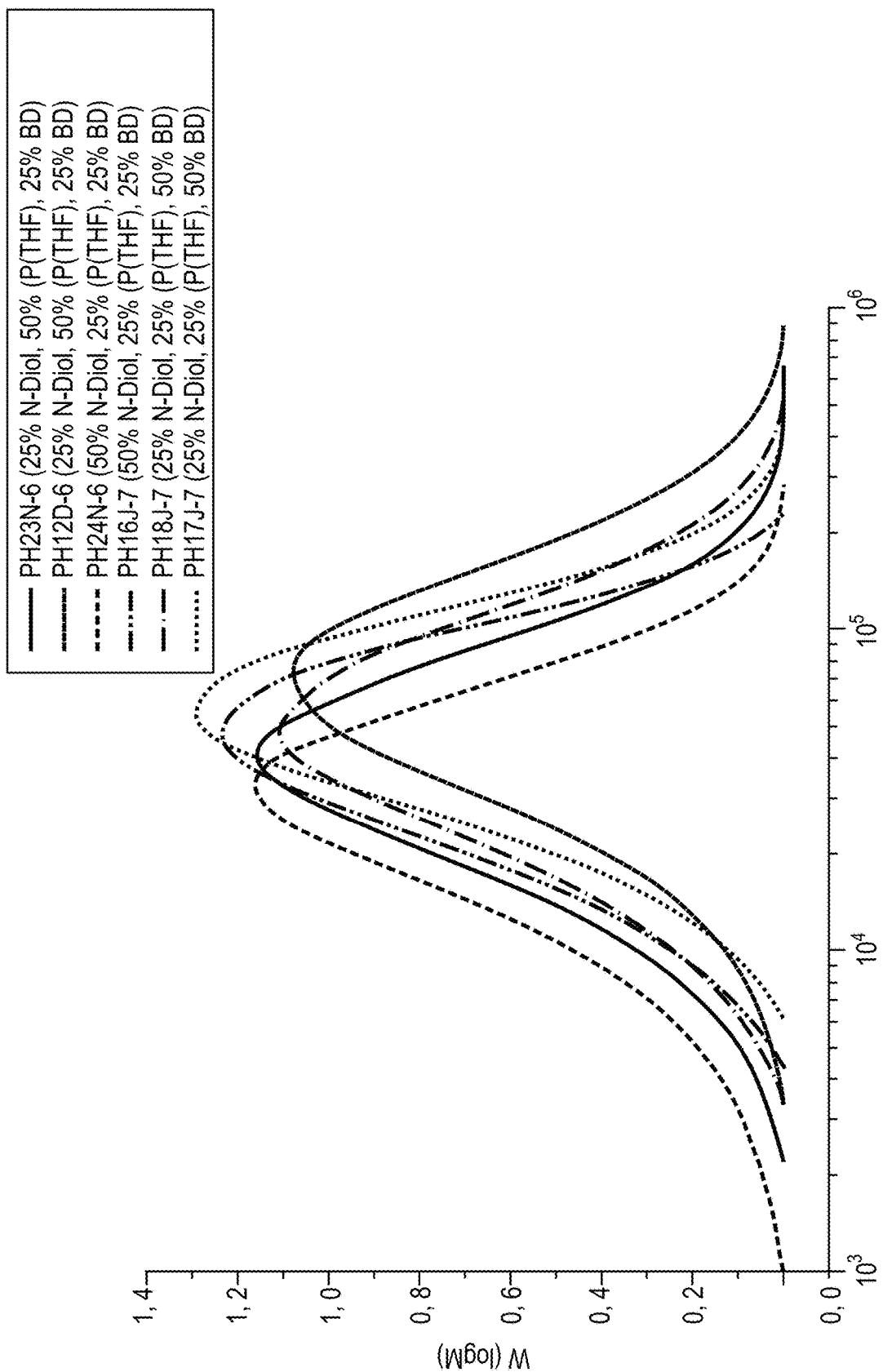
FIG. 9 shows the analysis by GPC (eluent: THF) of samples of PU-N+ produced by different sequences of addition of monomers.
Figure 10:
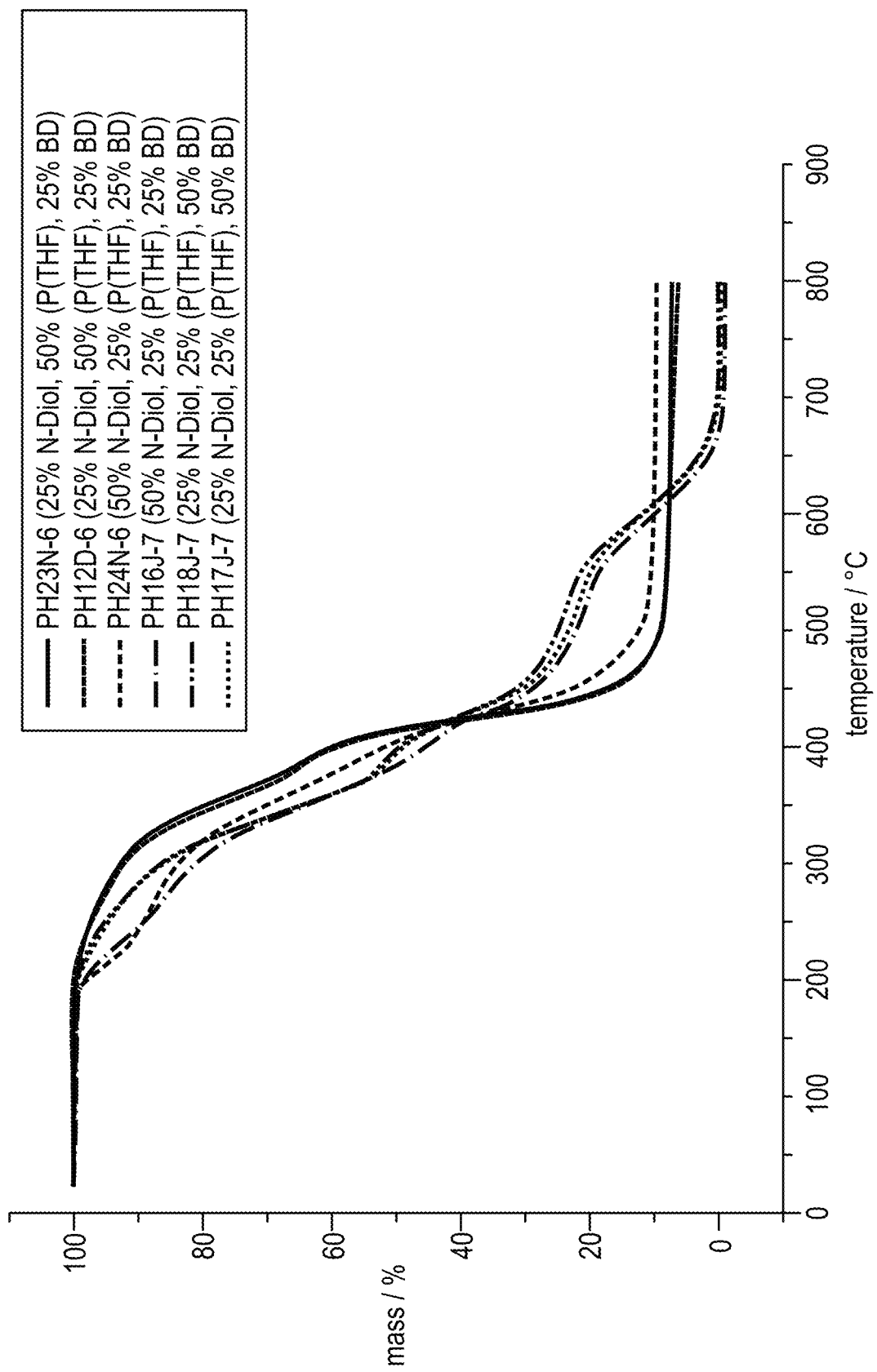
FIG. 10 shows the analysis by TGA (25-800° C., 10 K/min, $N_2$) of samples of PU-N produced by different sequences of addition of monomers.

Samples containing the PU-N product were analysed by GPC (FIG. 9) and TGA (FIG. 10).

As shown in FIG. 9, addition of P(THF) after BD (option 2) resulted in a higher molar mass.

The results to be seen from FIG. 9 are summarised in Table 5 below.

TABLE 5

| Sample | Mn [g/mol] | D |
|---|---|---|
| PH23N-6 | $2.3 \cdot 10^4$ | 2.1 |
| PH12D-6 | $4.3 \cdot 10^4$ | 2.1 |

TABLE 5-continued

| Sample | Mn [g/mol] | D |
|---|---|---|
| PH24N-6 | $1.6 \cdot 10^4$ | 2.2 |
| PH16J-7 | $3.1 \cdot 10^4$ | 1.7 |
| PH18J-7 | $3.1 \cdot 10^4$ | 2.0 |
| PH17J-7 | $4.0 \cdot 10^4$ | 1.6 |

Mn = molar mass; D = molecular mass [Da]

As to be seen from FIG. 10, the sequence of addition of monomers virtually showed no effect on the decomposition temperature.

The results to be seen from FIG. 10 are summarised in Table 6 below.

TABLE 6

| Sample | 5% Decomposition [° C.] |
|---|---|
| PH23N-6 | 278 |
| PH12D-6 | 271 |
| PH24N-6 | 213 |
| PH16J-7 | 221 |
| PH18J-7 | 246 |
| PH17J-7 | 251 |

Example 5: Quaternization of the N-Diol Containing PU Polymer

Chemicals

PU-N (as produced in Example 2); 1-bromobutane: CAS. 105-65-9, Merck, >98%; THF: technical grade, distilled before use.

Reaction

| Chemicals | M [g · mol$^{-1}$] | n [mol] | M [g] | D [g · cm$^{-3}$] | V [ml] |
|---|---|---|---|---|---|
| PU-N | | | 10 | | |
| 1-Bromobutane | 137.03 | 0.047 | 6.4 | 1.28 | 5 |
| THF | 72.11 | | | 0.889 | 30 |

Procedure 10 g PU-N was dissolved in 30 ml THF at 60° C. 5 ml 1-bromobutane was added. The reaction mixture was stirred at 60° C. for different time intervals to change the degree of quaternization. The quaternised polymer was precipitated in hexane and dried at 50° C. in vacuum. Yield: 96%.

The product PU-N+ was characterised by 1H-NMR spectroscopy.

Figure 6:
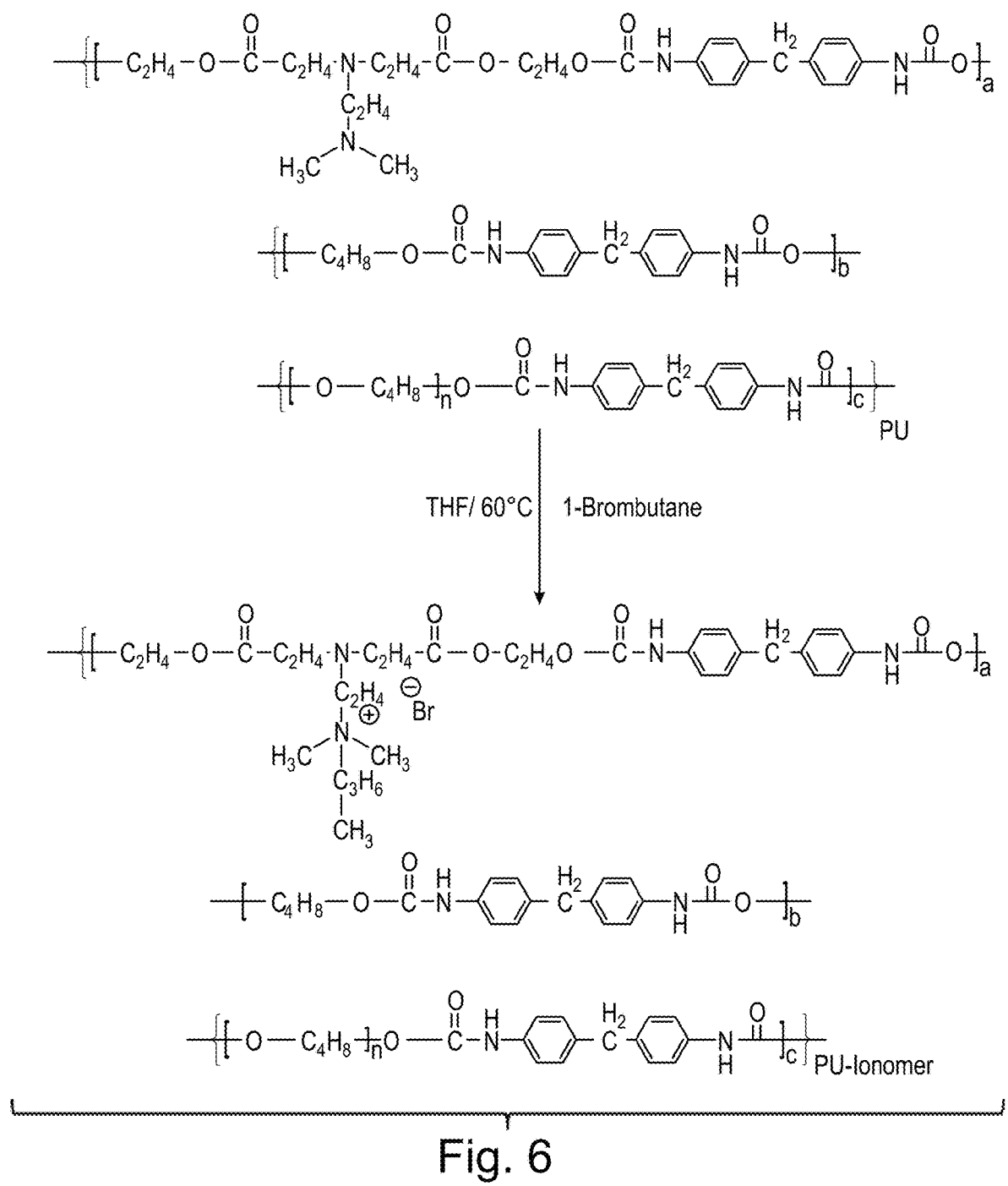
FIG. 6 shows a reaction scheme illustrating the quaternization of PU-N using 1-bromobutane, resulting in the production of PU-N+.
Figure 11:
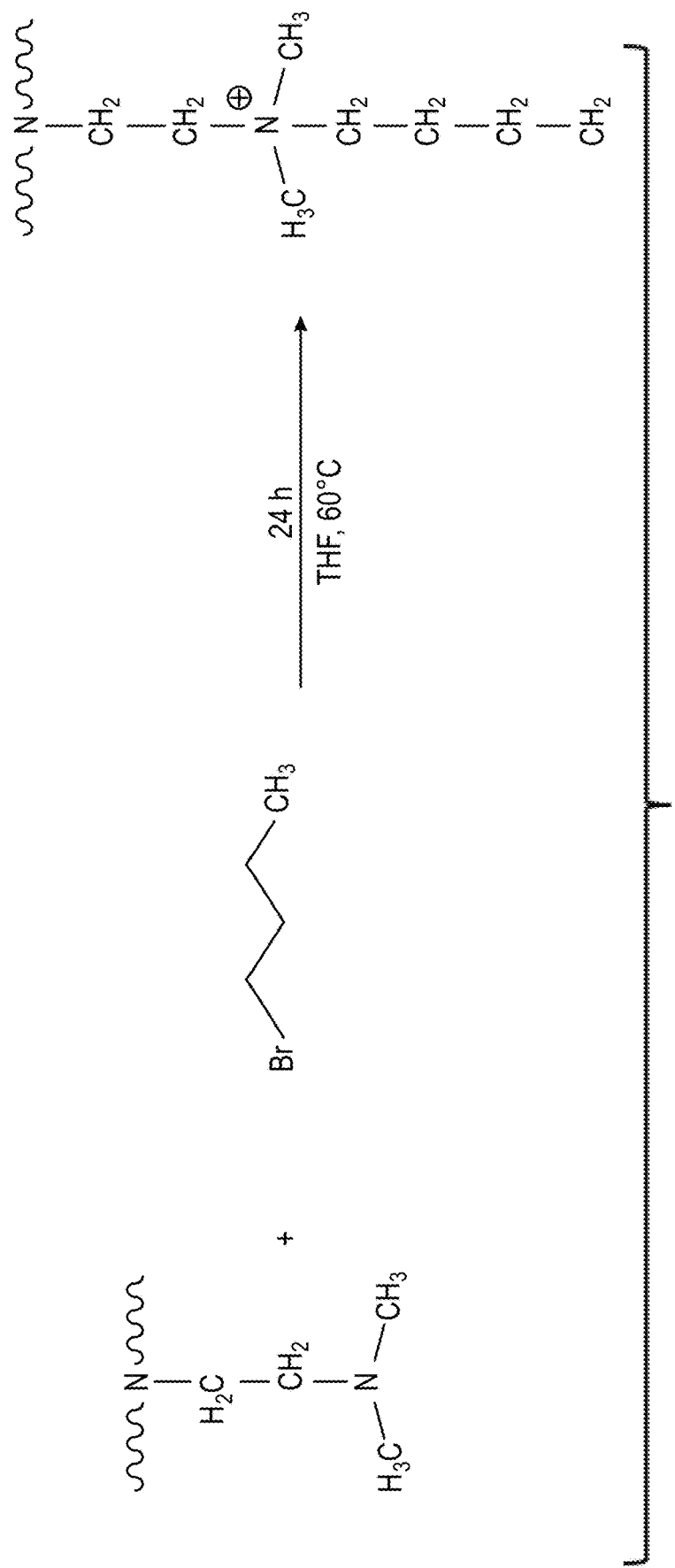
FIG. 11 illustrates the principle of quaternization of the alkylamino group contained in PU-N+.

A reaction scheme is shown in FIG. 6, and FIG. 11 further illustrates the principle of quaternization.

The extent of quaternization is exemplarily summarised in Table 7 below.

TABLE 7

| Sample | PU | Quaternisation [%] |
|---|---|---|
| PH06M-7_PU-N+_24h | PH16J-7_PU (50% N-diol, 25% P(THF), 25% BD) | 29 |
| PH07M-7_PU-N+_24h | PH17J_PU (25% N-diol, 25% P(THF), 50% BD) | 16 |
| PH07F-8_PU-N+ | (50% N-diol, 25% P(THF), 25% BD | 5 |

Example 6: Characterization of the Quaternised PU Polymer (PU-N+)

Figure 12:
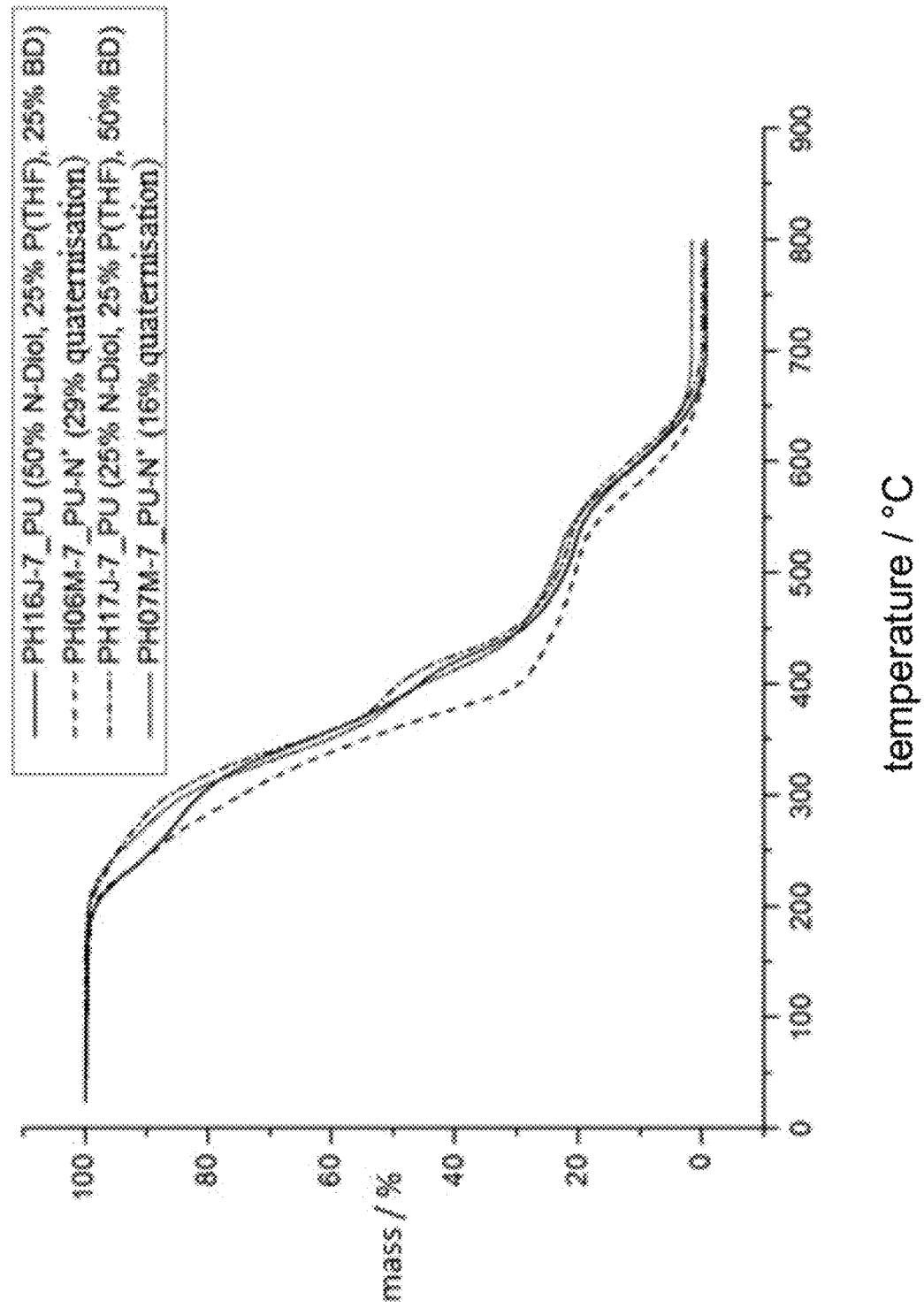
FIG. 12 shows the analysis by TGA (25-800° C., 10 K./min, air) of samples of PU-N and PU-N+.

Samples containing non-quaternised or quaternised PU polymer (i.e., PU-N or PU-N+) were analysed by TGA (FIG. 12). As shown, quaternization did not affect the decomposition temperature.

The results to be seen from FIG. 12 are summarised in Table 8 below.

TABLE 8

| Sample | 5% Decomposition [° C.] |
|---|---|
| PH16J-7_PU (50% N-diol, 25% P(THF), 25% BD) | 221 |
| PH06M-7_PU-N+_24h (29% quarternized) | 224 |
| PH17J-7_PU (25% N-diol, 25% P(THF), 50% BD) | 251 |
| PH07M-7_PU-N+_24h (16% quaternised) | 246 |

Example 7: Dynamic-Mechanical Thermoanalysis (DMTA)

Samples containing non-quaternised PU or quaternised PU polymer (i.e., PU-N or PU-N+) were analysed by DMTA; elastane served for comparison (FIGS. 13A-13E).

For DMTA, a Rheometric Scientific DMTA instrument was used.

In contrast to elastane (FIG. 13A), the PU polymer samples showed glass transition temperatures ($T_g$) of above 0° C., regardless of whether they were quaternised or not.

Figure 13A:
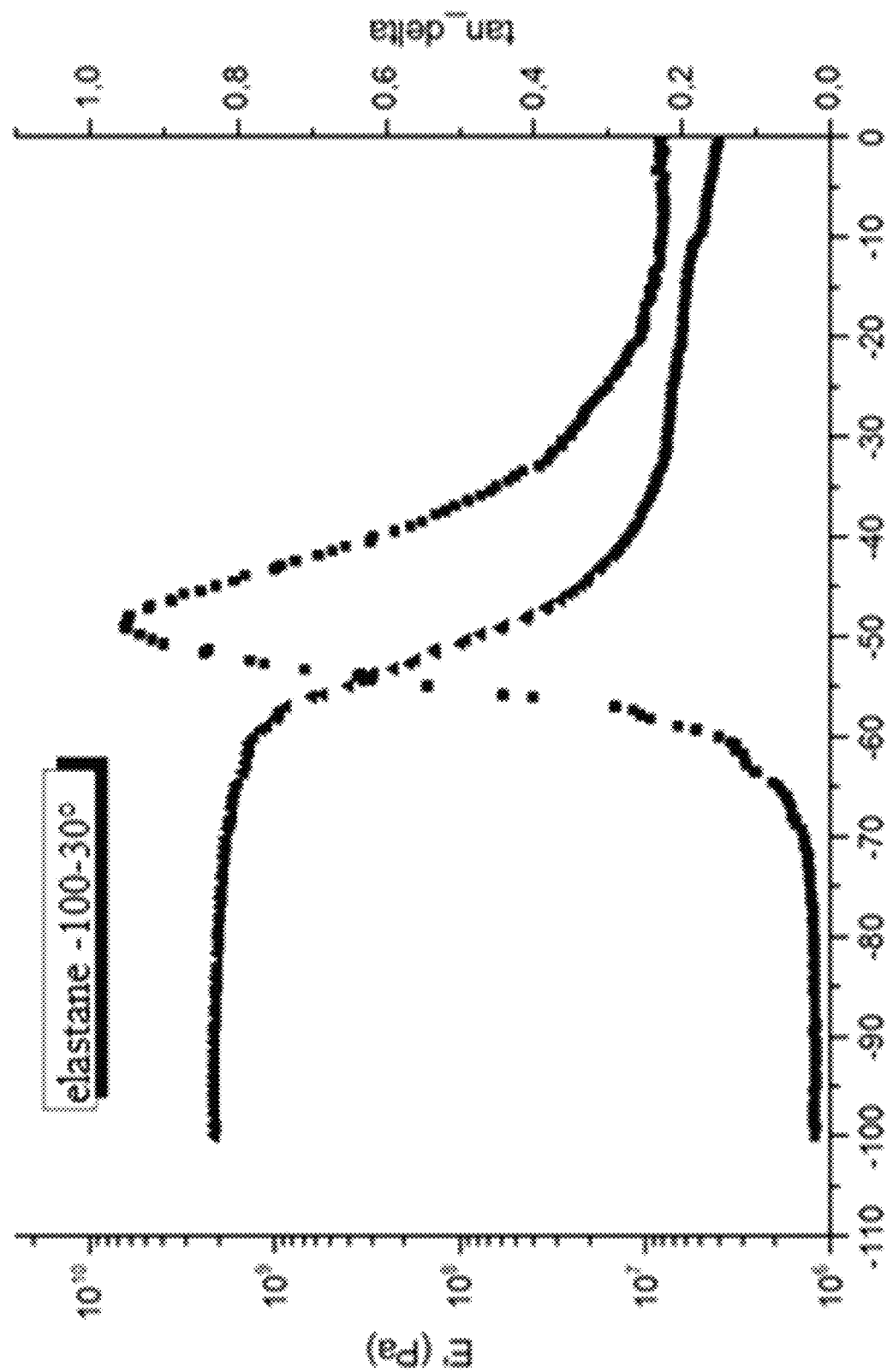
FIGS. 13A-13E show analyses by DMTA of elastane (13A), PU-N (13B), (13D), and PU-N+(13C), (13E).
Figure 13B:
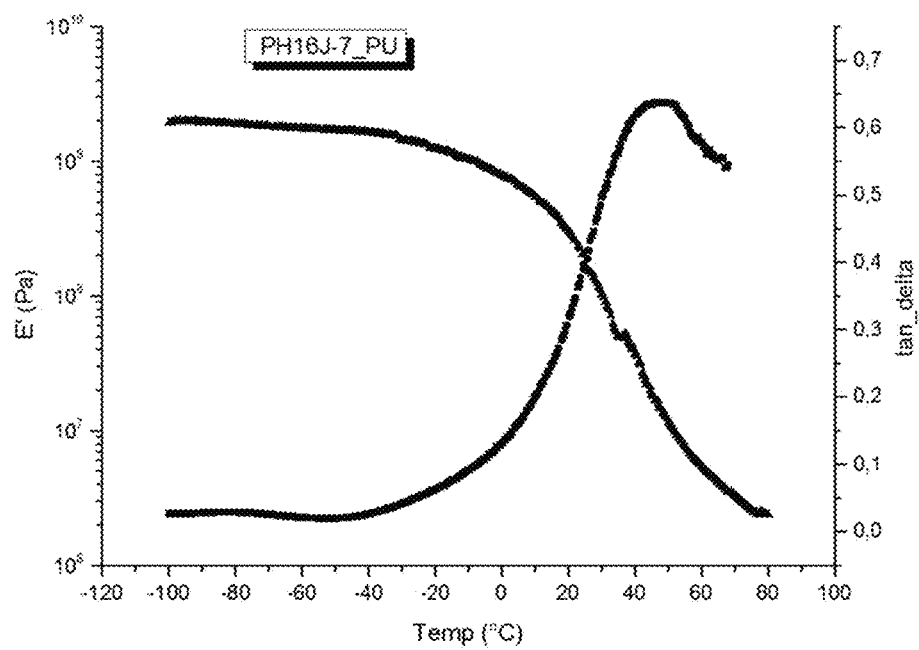

As furthermore shown, an increased amount of BD resulted in a higher glass transition temperature (FIG. 13B: $T_g$=40° C.; FIG. 13D: $T_g$=55° C.).

Figure 13C:
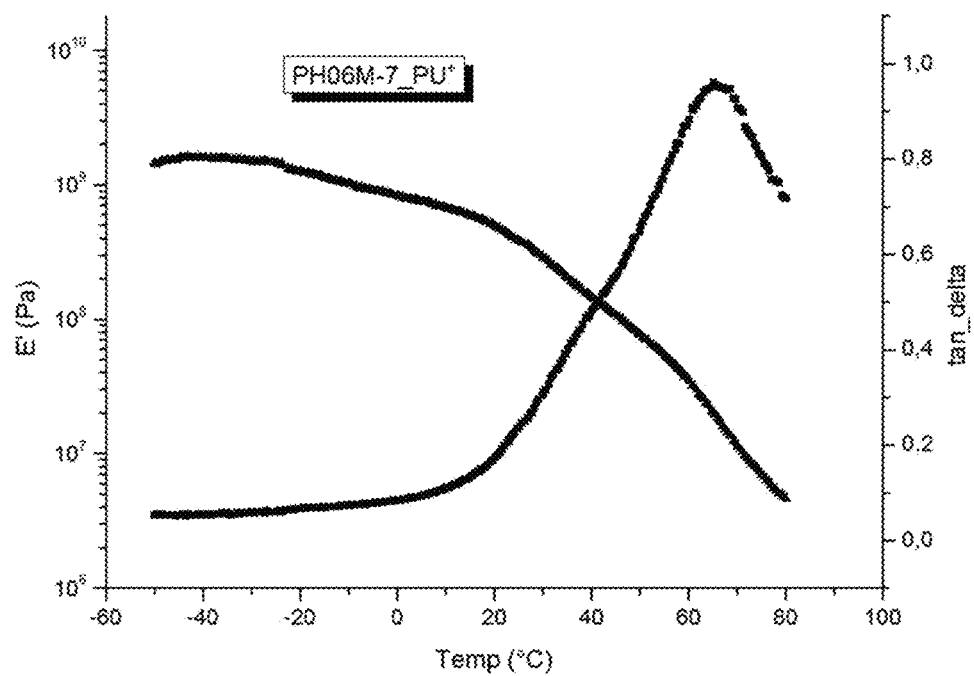
Figure 13D:
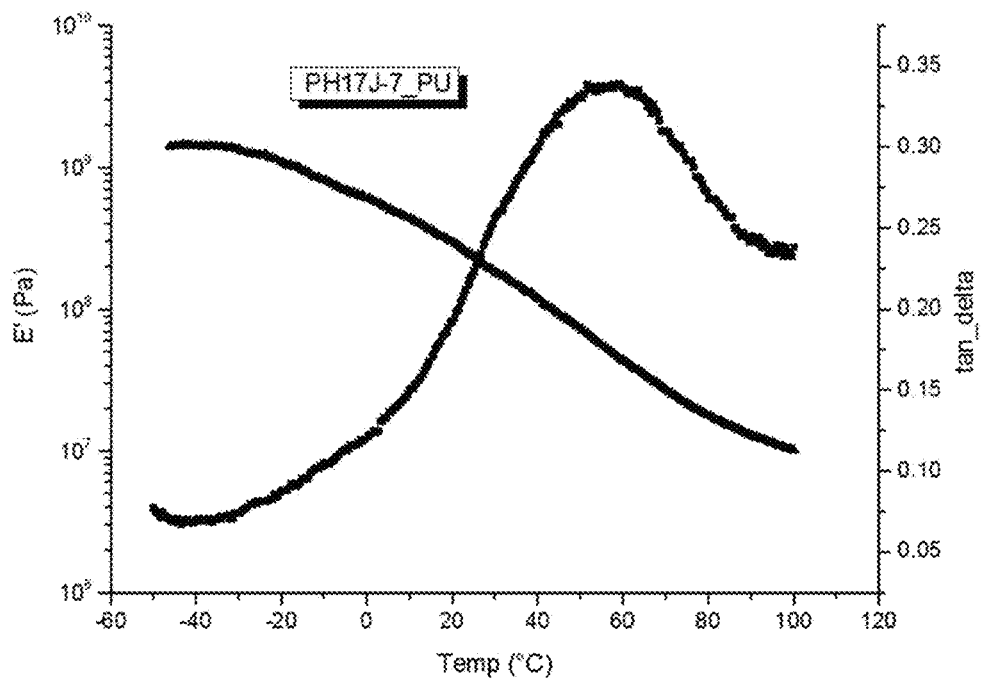
Figure 13E:
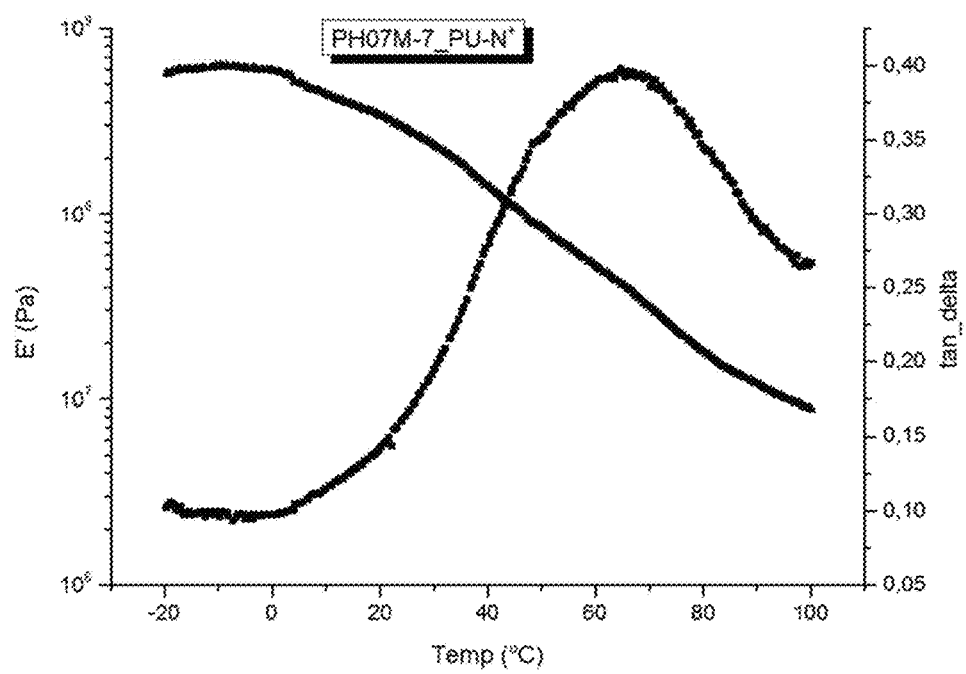

Finally, quaternization of PU-N (resulting in PU-N+) induced an increase in the glass transition temperatures observed with the non-quaternised PU-N (FIG. 13C: $T_{gi}$=70° C., i.e., >40° C.;

FIG. 13E: $T_{gi}$=70° C., i.e., >55° C.).

Example 8: Stress-Strain Test

Mechanical properties of the produced PU polymers were tested. For that purpose, samples of non-quaternised PU or quaternised PU polymer (i.e., PU-N or PU-N+) were analysed by a strain-stress test (tensile testing); elastane served for comparison.

For testing, a Zwick/Noell BT1-FR 0.5TN.D14 machine was used (pre-load: 0.01 N/mm test rate: 50 mm/min). Sample preparation: 1 g PU (PU-N or PU-N+) was dissolved in 10 ml HFIP (hexafluoroisopropanol) and dropped on a glass plate for making a film. The film was dried at room temperature for 24 h followed by drying at 45° C. in vacuum for 24 h. The films were cut to the dimensions (W: 5 mm, L: ≥40 mm) for mechanical testing.

As shown in FIGS. 14A-14B, PU-N+(FIG. 14B) showed a strain behaviour different from that of elastane (FIG. 14A).

Furthermore, quaternization induced a decrease in fracture strain, as shown in Table 9 below.

TABLE 9

| Sample | $E_{mod}$ [MPa] | Fracture strain dL [%] | Ratio of monomers |
|---|---|---|---|
| Elastane | 2.4 | 3,403 | |
| PH15D-6_PU | 12.5 | 1,566 | 50% P(THF), 50% BD |
| PH16J-7_PU | 37 | 1,388 | 50% N-Diol, 25% P(THF), 25% BD |
| PH06M-7_PU-N+ | 154 | 796 | 50% N-Diol, 25% P(THF), 25% BD 29% quaternisation |
| PH17J-7_PU | 95 | 1,025 | 25% N-Diol, 25% P(THF), 50% BD |
| PH07M-7_PU-N+ | 98 | 780 | 25% N-Diol, 25% P(THF), 50% BD 16% quaternisation |

$E_{mod}$ = modulus of elasticity; dL = delta length; % = weight %; film thickness: 180 ± 20 μm

Example 9: PU Polymer/Elastane Blends

The produced PU polymers were blended with elastane (commercially available). Mechanical properties were tested using a strain-stress test as described in Example 8.

As shown in FIGS. 15A-15B, a blend of 70% PU-N+ and 30% elastane (FIG. 15B) showed a strain behaviour different from that of elastane (FIG. 15A).

Furthermore, fracture strain and modulus of elasticity measured with different PU-N+/elastane blends are given in Table 10 below.

TABLE 10

| Sample | $E_{mod}$ [MPa] | Fracture strain dL [%] | Ratio of monomers |
|---|---|---|---|
| Elastane | 2.4 | 3,403 | |
| PH06M-7_PU-N+ | 154 | 796 | 50% N-Diol, 25% P(THF), 25% BD 29% quaternised |
| PH07M-7_PU-N+ | 98 | 780 | 25% N-Diol, 25% P(THF), 50% BD 29% quaternised |
| Blend_10% PH06M-7_PU-N+ | 3.4 | 3,044 | 10% PH06M-7_PU-N+ + 90% elastane |
| Blend_30% PH06M-7_PU-N+ | 7.1 | 2,413 | 30% PH06M-7_PU-N+ + 70% elastane |
| Blend_50% PH06M-7_PU-N+ | 15 | 1,601 | 50% PH06M-7_PU-N+ + 50 elastane |
| Blend_70% PH06M-7_PU-N+ | 31 | 1,097 | 70% PH06M-7_PU-N+ + 30% elastane |
| Blend_10% PH07M-7_PU-N+ | 3.4 | 3,060 | 10% PH07M-7_PU-N+ + 90% elastane |
| Blend_30% PH07M-7_PU-N+ | 6 | 2,331 | 30% PH07M-7_PU-N+ + 70% elastane |
| Blend_50% PH07M-7_PU-N+ | 14 | 1,710 | 50% PH07M-7_PU-N+ + 50% elastane |
| Blend_70% PH07M-7_PU-N+ | 39 | 1,301 | 70% PH07M-7_PU-N+ + 30% elastane |

$E_{mod}$ = modulus of elasticity; dL = delta length; % = weight %; film thickness: 160 ± 20 μm For comparison, fracture strain and modulus of elasticity measured with different PU-N (i.e., non-quaternised)/elastane blends are given in Table 11 below.

TABLE 11

| Sample | $E_{mod}$ [MPa] | Fracture strain dL [%] | Ratio of monomers |
|---|---|---|---|
| PH02M-7_PU | | | 50% N-Diol, 25% P(THF), 25% BD |
| Blend_10% PH02M-7_PU | 3.7 | 3,262 | 10% PH02M-7_PU + 90% elastane |
| Blend_30% PH02M-7_PU | 5.2 | 2,900 | 30% PH02M-7_PU + 70% elastane |
| Blend_50% PH02M-7_PU | 5.5 | 2,325 | 50% PH02M-7_PU-N + 50% elastane |
| Blend_70% PH02M-7_PU | 6.8 | 2,492 | 70% PH02M-7_PU-N + 30% elastane |
| Blend_90% PH02M-7_PU | 8.8 | 1,544 | 90% PH02M-7_PU-N + 10% elastane |

$E_{mod}$ = modulus of elasticity; delta length; % = weight %; film thickness: 140 ± 10 μm

Example 10: Relaxation Behaviour

Figure 16A:
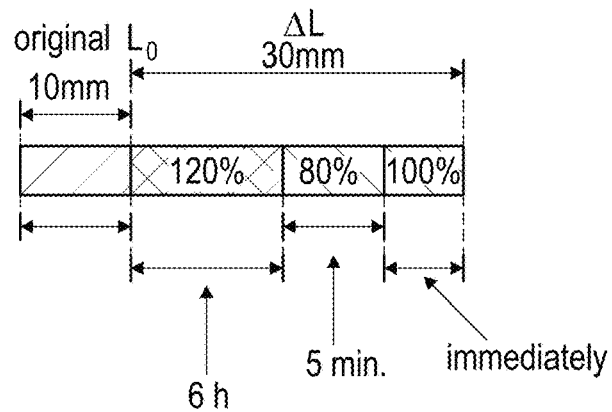
Figure 16B:
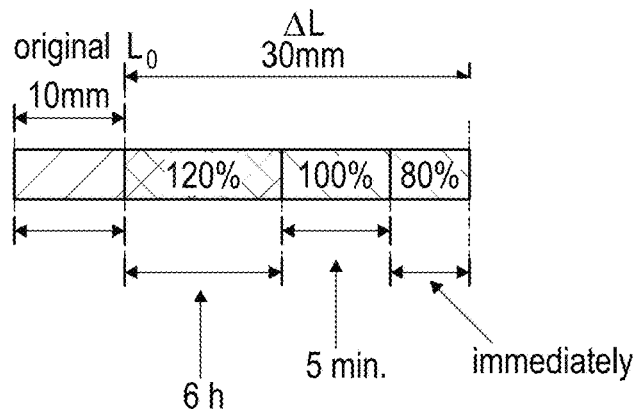

A sample of non-quaternised PU (PU-N) or of corresponding quaternised PU (PU-N+), 29% quaternization, was stretched from 10 mm (original sample length) to 40 mm (FIGS. 16A, and 16B). Upon release, both samples recovered their original sample lengths in about 6 hours. In doing so, approximately 180% recovery was achieved in about 5 min, after which the remaining 120% was recovered much more slowly. In this respect, the relaxation behaviour of PU-N and PU-N+ was almost the same.

Figure 16C:
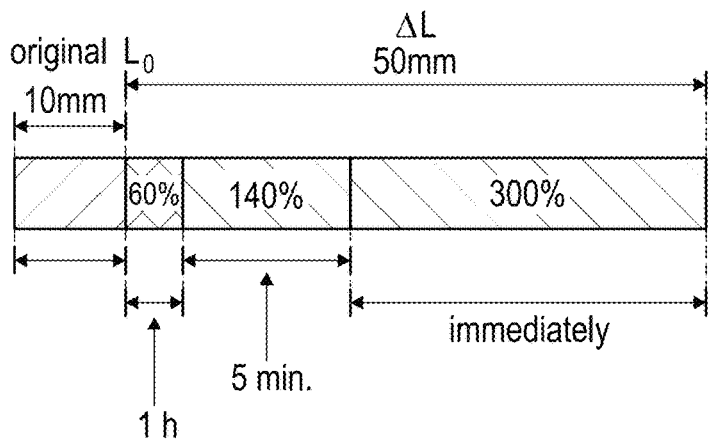
Figure 16D:
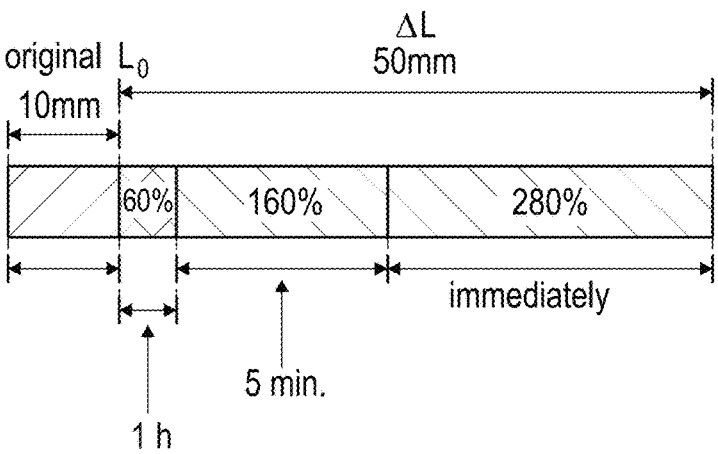

Similarly, samples of PU-N+ having different degrees of quaternization, namely 9% or 5%, were stretched from 10 mm to 50 mm (FIGS. 16C, and 16D). Upon release, 300% and 280% of the original sample length was recovered immediately, and further 140% and 160% was recovered after 5 min, respectively. Thus, approximately 90% total recovery was achieved within about 5 min.

Thus, the relaxation behaviour depends, at least partially, on the degree of quaternization.

The results to be seen from FIGS. 16A-16D are summarized in Table 12 below.

TABLE 12

| Sample | Immediate relax. [%] | Relaxation 1 [%/time] | Relaxation 2 [%/time] | Ratio of monomers |
|---|---|---|---|---|
| PH16J-7_PU | 100 | 80/5 min | 120/6 h | 50% N-diol, 25% P(THF), 25% BD |
| PH06M-7_PU-N+ (derived from PH16J-7_PU) | 80 | 100/5 min | 120/6 h | 50% N-diol, 25% P(THF), 25% BD 29% quaternisation |
| PH23M-7_PU-N+ (derived from PH02M-7_PU) | 300 | 140/5 min | 60/60 min | 50% N-diol, 25% P(THF), 25% BD 9% quaternisation |

TABLE 12-continued

| Sample | Immediate relax. [%] | Relaxation 1 [%/time] | Relaxation 2 [%/time] | Ratio of monomers |
|---|---|---|---|---|
| PH30M-7_PU-N+ (derived from PH02M-7_PU) | 280 | 160/5 min | 60/60 min | 50% N-diol, 25% P(THF), 25% BD 5% quaternisation |

Example 11: Relaxation Behaviour of PU Polymer/Elastane Blends

Non-quaternised PU (PU-N) or corresponding quaternised PU (PU-N+) having different degrees of quaternization (29%, 9% or 5%) were blended with elastane (commercially available), respectively. Samples were subjected to stretching-and-release similar to the description in Example 10 (stretching of samples from 10 to 50 mm).

The results are summarized in Tables 13 to 15 below.

TABLE 13

Blends of PU-N (PH02M-7_PU; 50% N-diol, 25% P(THF), 25% BD) and elastane.

| PU-N [wt %] | Elastane [wt %] | Immediate relaxation [%] | Relaxation 1 [%/time] | Relaxation 2 [%/time] |
|---|---|---|---|---|
| 10 | 90 | 450 | 30/5 min | 20/10-20 min |
| 30 | 70 | 430 | 40/5 min | 30/10-20 min |
| 50 | 50 | 420 | 50/5 min | 30/2 h |
| 70 | 30 | 410 | 60/5 min | 30/3 h |
| 90 | 10 | 390 | 80/5 min | 30/6 h |

Firstly, admixture of elastane to PU-N altered the relaxation behaviour of the individual PU-N and of elastane.

As to be seen from Table 13, the blends showed approximately 80 to 90% total recovery immediately after release, depending on the relative amounts of PU-N and elastane. Recovery of the remaining 10 to 20% took about 15 min to 6 hours, also depending on the relative amounts of PU-N and elastane. More generally, increased relative amounts of PU-N resulted in an increase in total relaxation time.

TABLE 14

Blends of PU-N+, 29% quaternisation (PH06M-7_PU-N+; 50% N-diol, 25% P(THF), 25% BD) and elastane.

| PU-N+ [wt %] | Elastane [wt %] | Immediate relaxation [%] | Relaxation 1 [%/time] | Relaxation 2 [%/time] |
|---|---|---|---|---|
| 10 | 90 | 440 | 20/5 min | 40/30-60 min |
| 30 | 70 | 400 | 40/5 min | 60/2 h |
| 50 | 50 | 340 | 100/5 min | 60/3 h |
| 70 | 30 | 280 | 120/5 min | 100/6 h |

As to be seen from Table 14, increased relative amounts of PU-N+ resulted in an increase of total relaxation time. Furthermore, compared to non-quaternised PU-N (Table 13), PU-N+ was associated with increased total relaxation times. Apart from that, PU-N+ with a high degree of quaternization (29%) does not provide any particular advantage over non-quaternised PU-N when used in blends with elastane.

TABLE 15

Blends of PU-N+, 9% quaternisation (PH23M-7_PU-N+; 50% N-diol, 25% P(THF), 25% BD) and elastane.

| PU-N+ [wt %] | Elastane [wt %] | Immediate relaxation [%] | Relaxation 1 [%/time] | Relaxation 2 [%/time] |
|---|---|---|---|---|
| 50 | 50 | 390 | 80/5 min | 30/30-60 min |
| 60 | 40 | 350 | 100/5 min | 50/30-60 min |
| 70 | 30 | 380 | 90/5 min | 30/30-60 min |

As to be seen from Table 15, blends with PU-N+ having a lower degree of quaternization (here: 9%) showed relaxation times of about 30 min to 1 h for all tested compositions. Apart from that, the relaxation behaviour is very similar to that of blends with non-quaternised PU-N, i.e., approximately 80% total recovery was achieved immediately.

TABLE 16

Blends of PU-N+, 5% quaternisation (PH30M-7_PU-N+; 50% N-diol, 25% P(THF), 25% BD) and elastane.

| PU-N+ [wt %] | Elastane [wt %] | Immediate relaxation [%] | Relaxation 1 [%/time] | Relaxation 2 [%/time] |
|---|---|---|---|---|
| 50 | 50 | 390 | 70/5 min | 40/30-60 min |
| 60 | 40 | 380 | 80/5 min | 40/30-60 min |
| 70 | 30 | 380 | 80/5 min | 40/30-60 min |

As to be seen from Table 16, the relaxation behaviour of blends with PU-N+ having a low degree of quaternization (here: 5%) is very similar to that of blends with PU-N+, 9% quaternization (Table 15), and of non-quaternised PU-N (Table 13).

TABLE 17

| Sample | N-Diol:P(THF):BD (molar ratio) | Degree of quaternisation [%] | Number average molar mass Mn [g/mol] | $T_g$ or $T_{g1}/T_{g2}$ [° C.] (from DMTA) | Degradation temperature [° C.] (from TGA) | $E_{mod}$ [MPa] | $\sigma_M$ [MPa] | dL [%] (pre-load: 0.01 N/mm; speed: 50 mm/min) |
|---|---|---|---|---|---|---|---|---|
| Elastane | | 0 | $7.54 \cdot 10^4$ | −50 | 243 | 2.4 | 27 | 3,403 |
| PH15D-6_PU | 0:1:1 | 0 | $3.06 \cdot 10^4$ | −25 | 230 | 12.5 | 33 | 1,566 |

TABLE 17-continued

| Sample | N-Diol: P(THF):BD (molar ratio) | Degree of quaternisation [%] | Number average molar mass Mn [g/mol] | $T_g$ or $T_{g1}/T_{g2}$ [°C.] (from DMTA) | Degradation temperature [°C.] (from TGA) | $E_{mod}$ [MPa] | $\sigma_M$ [MPa] | dL [%] (pre-load: 0.01 N/mm; speed: 50 mm/min) |
|---|---|---|---|---|---|---|---|---|
| PH16J-7_PU | 1:0.5:0.5 | 0 | | 40 | 185 | 37 | 35 | 1,388 |
| PH06M-7_PU-N+ (derived from PH16J-7_PU) | 1:0.5:0.5 | 24 h/29% | | 40/70 | 182 | 154 | 42 | 796 |
| PH23M-7_PU-N+ (derived from PH02M-7_PU) | 1:0.5:0.5 | 90 min/9% | | | | 29 | 12 | 968 |
| PH30M-7_PU-N+ (derived from PO2M-7_PU) | 1:0.5:0.5 | 45 min/5% | | | | 12 | 11 | 1,056 |
| Blend 30% PH16J-7_PU + 70% elastane | | | | | | 4 | 19 | 3,082 |
| Blend 50% PH16J-7_PU + 50% elastane | | | | | | 4.9 | 19 | 2,629 |
| Blend 70% PH16J-7_PU + 30% elastane | | | | | | 5.9 | 16 | 2,412 |
| Blend 10% PH02M-7_PU + 90% elastane | | | | | | 3.7 | 28 | 3,262 |
| Blend 30% PH02M-7_PU + 70% elastane | | | | | | 5.2 | 28 | 2,900 |
| Blend 50% PH02M-7_PU + 50% elastane | | | | | | 5.5 | 20 | 2,325 |
| Blend 70% PH02M-7_PU + 30% elastane | | | | | | 6.8 | 21 | 2,492 |
| Blend 90% PH02M-7_PU + 10% elastane | | | | | | 8.8 | 16 | 1,544 |
| Blend 50% PH23M-7_PU-N+ + 50% elastane | | | | | | 6.3 | 15 | 1,896 |
| Blend 60% PH23M-7_PU-N+ + 40% elastane | | | | | | 9.9 | 18 | 2,067 |
| Blend 70% PH23M-7_PU-N+ + 30% elastane | | | | | | 10.5 | 15 | 1,990 |
| Blend 50% PH30M-7_PU-N+ + 50% elastane | | | | | | 6.2 | 14 | 1,800 |
| Blend 60% PH30M-7_PU-N+ + 40% elastane | | | | | | 7.2 | 16 | 2,187 |
| Blend 70% PH30M-7_PU-N+ + 30% elastane | | | | | | 8.8 | 13 | 1,951 |

Example 12: Polymer Fibres/Filaments

A sample of quaternised PU polymer (PU-N+) (PH07F-8_PU-N+=–50% N-Diol, 25% P(THF)25% BD, 5% quaternised (5% N+)) was milled to a powder using an ultra-centrifugal mill ZM200. The milling machine had a sieve with pore diameter of 1 mm. Machine with any other pore diameter can also be used and sieve diameter is not important. Idea was to convert a mass of the polymer into a powder that can be easily fed to extruder for making filaments. Thereafter it was spun as a mono-filament using a twin screw extruder (process 11 from Thermo Scientific). The extruding filaments were continuingly passed through a trough having SiO2 powder to prevent any residual stickiness/tackiness of the filament and allowed storage of the filament, when it has been wound up into a roll without sticking to each other). Using this set up, the melt spinning of the PU ionomer into a mono-filament is easy, and a large scale production is possible.

An exemplary microscopical image of such filament is shown in FIG. 17 (500× magnification). The filaments are not transparent and have an opaque surface.

Mechanical properties of the spun filament were tested. For that purpose, the produced filament(s) were analyzed by a strain-stress test (tensile testing). For testing, a Zwick/Noell BT1FR0.5TN.D14 machine was as used. (Preload: 0.1 kPa, test rate: 50 mm/min). The filament had a diameter of 280+/–30 and the filament was subjected to tensile testing The following results were achieved:

| Sample | $E_{mod}$/ MPa | Fracture strain dL [%] | F (max)/ MPa | Monomer ratio |
|---|---|---|---|---|
| PH07F-8_PU-N+_filament_with SiO₂ powder | 2.5 | 1100 | 29 | 50% N-Diol, 25% P(THF), 25% BD, 5% N+ |

$E_{mod}$ = modulus of elasticity; dL = delta length; % = weight percent; filament diameter = 208 +– 30 μm The results of the strain-stress test are shown in FIG. 18.

The relaxation behavior of such filaments is shown in FIG. 19. For such relaxation behavior, a filament of quaternised polyurethane polymer was stretched from 10 mm (original filament length) to 50 mm. Upon release, the filament recovered its original sample length in approximately 35-65 min.

In summary, in this example, the inventors have shown that polyurethane-ionomer can be reproducibly spun into filaments the tackiness of which can be prevented by dusting with SiO₂-powder or a similar powder or a suitable oil. The powder does not interfere with the relaxation behavior.

The invention claimed is:

1. A compression product comprising an elastic component or material, the elastic component or material having a delayed continuous relaxation behavior, the elastic component or material being capable of applying a compression or a supporting force or a local pressure to a part of the body of a subject, the elastic component or material furthermore being capable of passing through a first phase during which the component or material is expanded, a second phase during which the component or material relaxes without recovering its original shape, and a third phase during which the component or material recovers its original shape with successive deceleration, wherein relaxation is self-initiated in the absence of an external stimulus;
   wherein recovery of the original shape does not proceed linearly over time, but is more and more delayed; and
   wherein the compression product is selected from the group consisting of a compression hosiery, a compression stocking, sock, knee sock, tights, panty hose, maternity panty hose, a compression knee guard, a compression arm sleeve, a compression waist attachment, belt or girdle, a compression bandage, a body-supporting bandage, an orthosis, a prosthesis liner, a compression wound dressing, a compression plaster or patch, and a compression garment.

2. The compression product, according to claim 1, comprising an elastic component or material comprising:
   (a) a non-quaternized polyurethane (PU) polymer containing N-diol (PU-N);
   and/or
   (b) a quaternized polyurethane (PU) polymer or ionomer containing quaternized N-diol (PU-N+);
   and, optionally,
   (c) elastane.

3. The compression product according to claim 1, comprising an elastic component or material comprising a non-quaternized PU polymer and, optionally, elastane.

4. A method of providing compression to a subject in need of such compression, wherein said method comprises applying to a body part of the subject a compression product according to claim 1 in a field of phlebology, orthopaedics, foot care, surgery, post-surgery care, trauma management, wound care, or sports; or for treatment or prevention or management of impaired musco-venous pump performance, compromised venous circulation, venous insufficiency, oedema, phlebitis, thrombosis, venous embolism, lymphoedema, ulcer, aching legs, varicose veins, spider veins, or the "economy class syndrome" (ECS).

5. A polyurethane (PU) polymer having a delayed continuous relaxation behavior, wherein relaxation is initiated autonomously or spontaneously in the absence of an external stimulus, wherein the delayed relaxation behavior is delayed in respect of duration of the immediate relaxation phase and/or successive compression phase.

6. The polyurethane (PU) polymer according to claim 5, the PU polymer containing at least one N-diol monomer component.

7. The polyurethane (PU) polymer according to claim 6, which is a non-quaternized PU polymer (PU-N).

8. The polyurethane (PU) polymer according to claim 6, which is a quaternized PU polymer (PU-N+) or a quaternized PU ionomer (PU-N+).

9. The polyurethane (PU) polymer according to claim 6, wherein the N-diol monomer component is derived from bis(2-hydroxyethyl)-3,3'-((2-(dimethylamino)ethyl) azanediyl)-dipropionate or N',N'-bis(3-(2-hydroxyethoxy)-3-oxopropyl)-N,N-dimethylethylendiamine.

10. The polyurethane (PU) polymer according to claim 6, comprising a first molecular unit consisting of a N-diol monomer component and an isocyanate monomer component, a second molecular unit consisting of a 1,4-butanediol monomer component and an isocyanate monomer component, and a third molecular unit consisting of a P (THF) monomer component and an isocyanate component.

11. The polyurethane (PU) polymer according to claim 10, the relative amounts of N-diol, P(THF) and 1,4-butanediol monomer components being about 50:25:25%.

12. The polyurethane (PU) polymer according to claim 8, wherein the quaternized PU polymer or ionomer comprises an amount of quaternized N-containing groups of up to about 15% of ionic groups, related to the total moles of the PU polymer.

13. The polyurethane (PU) polymer according to claim 5, having a glass transition temperature $T_g$ of between about 20 and 60° C.

14. A blend comprising:
    (a) a non-quaternized polyurethane (PU) polymer containing N-diol (PU-N);
    and/or
    (b) a quaternized polyurethane (PU) polymer or ionomer containing quaternized N-diol (PU-N+);
    and
    (c) elastane.

15. The blend according to claim 14, comprising between about 5 and 40% (by weight) non-quaternized PU polymer, and between about 60 and 95% (by weight) elastane.

16. A method for producing a compression product; an elastic component or material; an elastic fibre, filament, thread, or yarn; or a compressive base fabric; wherein said method comprises the use of a polyurethane (PU) polymer having a delayed continuous relaxation behavior, wherein relaxation is initiated autonomously or spontaneously in the absence of an external stimulus or the use of a blend according to claim 14.

17. A process for producing a polyurethane (PU) polymer containing N-diol, the PU polymer containing at least one N-diol monomer component, comprising the steps of:
    (i) Preparation of a quaternizable N-diol;
    (ii) Preparation of a PU polymer containing a quaternizable N-diol as produced in step (i);
    and, optionally,
    (iii) Quaternization of the PU polymer produced in step (ii).

18. The process according to claim 17, wherein the N-diol monomer component is derived from bis(2-hydroxyethyl)-3,3'-((2-(dimethylamino)ethyl)azanediyl)-dipropionate or N',N'-bis(3-(2-hydroxyethoxy)-3-oxopropyl)-N,N-dimethylethylendiamine.

19. A polyurethane (PU) polymer containing N-diol produced in accordance with a process according to claim 17.

* * * * *